(12) United States Patent
Stålhandske et al.

(10) Patent No.: US 10,190,149 B2
(45) Date of Patent: Jan. 29, 2019

(54) KIT AND METHOD FOR MEASURING THE ACTIVITY OF DEOXYNUCLEOSIDE KINASE

(71) Applicant: Biovica International AB, Uppsala (SE)

(72) Inventors: Per Stålhandske, Knivsta (SE); Johan Lennerstrand, Uppsala (SE)

(73) Assignee: Biovica International AB, Uppsala (SE)

(*) Notice: Subject to any disclaimer, the term of this patent is extended or adjusted under 35 U.S.C. 154(b) by 2 days.

(21) Appl. No.: 15/243,764

(22) Filed: Aug. 22, 2016

(65) Prior Publication Data

US 2017/0029867 A1    Feb. 2, 2017

Related U.S. Application Data

(62) Division of application No. 13/697,279, filed as application No. PCT/SE2011/050605 on May 13, 2011, now Pat. No. 9,429,518.

(30) Foreign Application Priority Data

May 14, 2010 (SE) ..................... 1050473

(51) Int. Cl.
*C12Q 1/68* (2018.01)
*C12Q 1/48* (2006.01)
(Continued)

(52) U.S. Cl.
CPC ........... *C12Q 1/485* (2013.01); *C12N 9/1252* (2013.01); *G01N 21/6428* (2013.01); (Continued)

(58) Field of Classification Search
None
See application file for complete search history.

(56) References Cited

U.S. PATENT DOCUMENTS 5,189,019 A   2/1993 Palladino et al.
5,273,879 A   12/1993 Goodman et al.
(Continued)

FOREIGN PATENT DOCUMENTS

EP   1 385 005 A1   1/2004
JP   2009-268381 A   11/2009
(Continued)

OTHER PUBLICATIONS

Staub, M. et al. (1988) "DNA Synthesis and Nucleotide Metabolism in Human Tonsillar Lymphocyte Subpopulations," Acta Otolaryngol (Stockh) Suppl. 454:118-124.
(Continued)

*Primary Examiner* — Joseph G. Dauner
(74) *Attorney, Agent, or Firm* — Foley & Lardner LLP

(57) ABSTRACT

The present invention relates to a kit comprising a DNA-dependant DNA polymerase and at least one natural deoxynucleoside and to a kit comprising a DNA-dependent DNA polymerase and a detection system comprising a DNA template molecule, a DNA primer molecule, and a fluorescent moiety capable of being displaced from, or bound to, dsDNA synthesized by said DNA-dependent polymerase. It further relates to A method for measuring deoxynucleoside kinase activity in a sample characterized by; (i) contacting the sample, in a container, with a reaction mix comprising a DNA-dependent DNA polymerase, at least one deoxynucleoside and a detection system comprising a DNA template molecule, a DNA primer molecule, and a fluorescent moiety capable of being incorporated in, displaced from, or bound to dsDNA synthesized by said DNA dependent polymerase; (ii) incubating said container; (iii) measuring the signal from the fluorescent moiety; and correlating the signal from the fluorescent moiety to the deoxynucleoside kinase activity in the sample.

11 Claims, 13 Drawing Sheets

Specification includes a Sequence Listing.

(51) Int. Cl.
 C12N 9/12 (2006.01)
 G01N 21/64 (2006.01)
(52) U.S. Cl.
 CPC ............... C12Y 207/07007 (2013.01); G01N 2333/9126 (2013.01); G01N 2333/91235 (2013.01)

(56) References Cited

U.S. PATENT DOCUMENTS

| | | | |
|---|---|---|---|
| 5,321,010 | A | 6/1994 | Connolly et al. |
| 5,328,827 | A | 7/1994 | Bishop et al. |
| 6,001,566 | A | 12/1999 | Canard et al. |
| 9,429,518 | B2 | 8/2016 | Stålhandske et al. |
| 2008/0166772 | A1 | 7/2008 | Hollinger et al. |
| 2008/0248472 | A1 | 10/2008 | Gronowitz |
| 2009/0197254 | A1 | 8/2009 | Lee |

FOREIGN PATENT DOCUMENTS

| | | |
|---|---|---|
| WO | WO 1991/04322 A1 | 4/1991 |
| WO | WO 1995/12313 A1 | 5/1995 |
| WO | WO-03/038042 | 5/2003 |
| WO | WO-2006/081462 | 8/2006 |
| WO | WO 2006/091158 A1 | 8/2006 |
| WO | WO 2008/024052 A1 | 2/2008 |
| WO | WO 2009/063254 A2 | 5/2009 |
| WO | WO 2010/015844 A1 | 2/2010 |
| WO | WO 2010/036359 A2 | 4/2010 |

OTHER PUBLICATIONS

International Search Report (ISA/SE) for International Application No. PCT/SE2011/050605, dated Sep. 15, 2011, 4 pages.
Eriksson et al., "Structure and function of cellular deoxyribonucleoside kinases," Cell. Mol. Life Sci. 59: 1327-1346 (2002).
Topolcan et al., "The role of thymidine kinase in cancer diseases," Expert Opin. Med. Diagn 2(2): 129-141 (2008).
Extended European Search Report for European Application No. 11780890.7, dated Oct. 25, 2013, 10 pages.
Massare, et al., "Inhibition of herpesvirus-induced thymidine kinase and DNA polymerase by β-hydroxynorvaline", FEBS Letters, vol. 223, No. 1, pp. 122-126, (1987).
Ohrvik, et al., "Sensitive nonradiometric method for determining thymidine kinase 1 activity", Clinical Chemistry, 50: 9, pp. 1597-1606, (2004).
Parker, et al., "Effects of 2-chloro-9-(2-deoxy-2-fluoro-β-D-arabinofuranosyl) adenine on K562 cellular metabolism and the inhibition of human ribonucleotide reductase and DNa polymerases by its 5"-Triphosphate", Cancer Research, 51: pp. 2386-2394, (1991).
Stalhandske, et al., "Homogeneous assay for real-time and stimultaneous detection of thymidine kinase 1 and deoxycytidine kinase activities", Analytical Biochemistry, 432: pp. 155-164, (2013).
Restriction Requirement for U.S. Appl. No. 13/697,279 dated Nov. 12, 2014, 6 pages.
Non-Final Office Action for U.S. Appl. No. 13/697,279 dated Jan. 2, 2015, 11 pages.
Final Office Action for U.S. Appl. No. 13/697,279 dated Jun. 19, 2015, 14 pages.
Advisory Action for U.S. Appl. No. 13/697,279 dated Oct. 15, 2015, 10 pages.
Notice of Allowance for U.S. Appl. No. 13/697,279 dated Apr. 18, 2016, 10 pages.
Wittwer et al. BioTechniques. 1997. 22: 130-138.
Gammon et al. "A method for quantification of nucleotides and nucleotide analogues in thymidine kinase assays using lanthanum phosphate coprecipitation" Analytical Biochemistry, vol. 369, 2007, pp. 80-86.
Holland et al., "Detection of specific polymerase chain reaction product by utilizing the 5'-3' exonuclease activity of Thermus aquaticus DNA polymerase" PNAS, vol. 88, 1991, pp. 7276-7280.
Higuchi et al., "Kinetic PCR Analysis: Real time monitoring of DNA Amplification Reactions" Biotechnology, vol. 11, 1993, pp. 1026-1030.
Lotafi et al. "The pattern of deoxycytidine- and deoxyguanosine kinase activity in relation to messenger RNA expression in blood cells from untreated patients with B-cell chronic lymphocytic leukemia" Biochemical Pharmacology, vol. 71, 2006, pp. 882-890.
Schulze et al., "Derivation, maintenance and characterization of Rat Embryonic Stem Cells in Vitro" Methods in Molecular Biology, vol. 329, 2006, pp. 45-47.
Valasek et al., "The power of real-time PCR" Adv. Physiol Educ., vol. 29, 2005, pp. 151-159.
Al-Taher A et al. (2000), "Global cDNA amplification combined with real-time RT-PCR: accurate quantification of multiple human potassium channel genes at the single cell level", Yeast 2000; 17: 201-210.
Amblar M et al. (2001), "Biochemical Analysis of Point Mutations in the 5'-3' Exonuclease of DNA Polymerase I of Streptococcus pneumonia", The Journal of Biological Chemistry, vol. 276, No. 22, Jun. 1, 2001, pp. 19172-19181.
Application Note (2011): "Accurate and sensitive mutation detection and quantification using TaqMan Mutation Detection Assays for disease research", TaqMan by Life Technologies Corporation, 8 pages.
Applied Biosystems—Support: PCR Optimization: Reaction Conditions and Components, Retrieved from http://www.appliedbiosystems.com/sup . . . on Aug. 14, 2015, 7 pages.
Biopharmaceutical glossaries & terminology: Biopharmaceutical Assays & Screening glossary & taxonomy, last revised Oct. 5, 2010, Retrieved at http://genomicglossaries.com/content/p . . . on Mar. 8, 2015.
Bresnick B et al. (1964), "End-Product Inhibition of Thymidine Kinase Activity in Normal and Leukemic Human Leukocytes", Cancer Res 1964, 24:841-846.
Gevertz J L et al. (2005), "Mathematical Model of Real-Time PCR Kinetics", Biotechnol Bioeng. 2005, 92(3):346-355.
Ives D H et al. (1963), "Feedback Inhibition of Thymidine Kinase by Thymidine Triphosphate", The Journal of Biological Chemistry, vol. 238, No. 4, Apr. 1963, pp. 1467-1474.
Michaelis-Menten Equation—Interactive Graph—PhysiologyWeb, Posted and Last Updated 2014, Retrieved from http://www.physiologyweb.com/calculators/michaelis_menten_equation_interactive_graph.html in 2016, 3 pages.
Mizrahi V et al. (1996), "Deoxy- and dideoxynucleotide discrimination and identification of critical 5' nuclease domain residues of the DNA polymerase I from Mycobacterium tuberculosis", Nucleic Acids Research, 1996, vol. 24, No. 24, pp. 4845-4852.
Morimyo M et al. (1993), "A simple and rapid amplification procedure for cDNA cloned in dephosphorylated plasmid", Nucleic Acids Research, 1993, vol. 21, No. 7, 1679-1680.
Reed M C et al. (2010), "The biological significance of substrate inhibition: A mechanism with diverse functions", Bioessays 32: 422-429.
Xu Y et al. (1997), "Biochemical and Mutational Studies of the 5'-3' Exonuclease of DNA Polymerase I of Escherichia coli", J. Mol. Biol., 268, pp. 284-302.
Xu Y et al. (2000), "Coordination between the Polymerase and 5'Nuclease Components of DNA Polymerase I of Escherichia coli", The Journal of Biological Chemistry, vol. 275, No. 27, Jul. 7, 2000, pp. 20949-20955.

KIT AND METHOD FOR MEASURING THE ACTIVITY OF DEOXYNUCLEOSIDE KINASE

CROSS-REFERENCE TO RELATED APPLICATIONS

This application is a divisional of U.S. patent application Ser. No. 13/697,279, filed Nov. 9, 2012, which is a national stage application under 35 U.S.C. § 371 of International Application No. PCT/SE2011/050605, filed May 13, 2011, which in turn claims priority to Swedish Patent Application No. 1050473-6, filed May 14, 2010, the contents of which are hereby incorporated by reference in their entireties into the present disclosure.

SEQUENCE LISTING

The instant application contains a Sequence Listing which has been submitted electronically in ASCII format and is hereby incorporated by reference in its entirety. Said ASCII copy, created on Aug. 23, 2018, is named 102796-0171$_{13}$ Sequence$_{13}$ Listing.txt and is 5,898 bytes in size.

TECHNICAL FIELD

The present invention relates to kit and method for homogenous, i.e. non-solidphase, determination in real-time of one or several deoxyribonucleoside kinases in a sample for the diagnosis of disease, disorder, infection, both viral and bacterial, or cancer.

BACKGROUND TO THE INVENTION

Deoxyribonucleoside Kinases

In eukaryotic cells there exist at least three deoxyribonucleoside kinases, thymidine kinase 1 and 2, TK and TK2, deoxycytidine kinase, dCK and deoxyguanosine kinase, dGK.

There exist two human gene loci encoding the two different thymidine kinases. Thymidine kinase can be found in the cytosol of the cell. Thymidine kinase 2 is localized in the mitochondrion and participates in mitochondrial DNA synthesis. TK2 has a different amino acid sequence, substrate specificity and expression profile from thymidine kinase 1.

Thymidine kinase 1 activity is most pronounced from the end of the G1 phase and through the S phase of the cell cycle. TK and dCK are responsible for regulating the pools of TTP and dCTP in the cell through the salvage pathway. The TK enzyme is the enzyme that catalyses the transformation of thymidine to thymidine monophosphate (TMP) in the presence of adenosine triphosphate (ATP).

Deoxycytidine kinase, activity is found during the whole cell cycle and is primarily identified in cells of lymphoid origin. TK2 is located in the mitochondrion and has an almost equal affinity for dC as dCK.

Diagnosis of Disease

In the early 1980-ies it was shown that thymidine kinase activity not only can be detected in serum from patients affected with various tumour diseases but varied extensively from healthy human individuals that normally exhibit very low TK activity The use of TK as a single tumour marker for the diagnosis and prognosis of haematological cancer diseases is now widely accepted. In certain instances TK has shown direct diagnostic capabilities.

The activity of TK and other deoxyribonucleoside kinases was early correlated to disease, which is summarised in reviews by Eriksson et al. 2002 and by Topolcan and Holubec 2008.

TK2 has been connected to mitochondrial diseases.

Assays for Determination of Deoxyribonucleoside Kinases

Radioactive substrates, such as $^3$H-thymidine, have been widely used for determination of TK and dCK activity in the filter-binding assays. For routine clinical diagnostics, radioactive based assays are not an attractive option.

During the last years several attempt has been made to develop non-radioactive based assays, all of these better in one way or the other. Below follow a set of methods, assays and reagent compositions used in the detection of different deoxyribonucleoside kinases.

In EP1385005 a non-radioactive TK activity based assay based on competitive mono-phosphorylation of azidothymidine (AZT) is presented. This technology has been further developed into an automated 2-step LIAISON® luminometric diagnostic assay by Diasorin S.r.I. In this two-step assay, AZT is first phosphorylated to monophosphorylated AZTMP by the TK present in a sample. Then luminescence is next detected from AZTMP conjugated to isoluminol (AZTMP-ABEI) which is competing with the TK phosphorylated AZTMP on solid surface substrate bound anti-AZ-TMP antibodies. The major drawback of this two-step assay is the limited dynamic reading. Another drawback is the use if modified nucleoside substrate in place of the natural thymidine.

In WO2009/063254 a semi-homogenous method for the determination of TK activity in a sample by the use of monophosphorylated Br-dU which is separated by HPLC and detected by UV is disclosed. Disadvantage with this method is that the reaction is done with a modified substrate and the detection is done in a separate step.

US2008/248472 discloses a solid phase assay utilizing complementation of TK activity, in a sample, by deoxyribonucleoside kinases in the reagent mix for production of Br-dUTP, which is a derivative of the natural TTP. The Br-dUTP is subsequently incorporated by primer extension using a RNA-dependent DNA polymerase. The solid phase bound RNA template is build of the monomer rA and is 200-400 monomers long, and attached to solid phase. Incorporated [Br]U is detected in the second step using an anti-[Br]dU alkaline phosphatase conjugated antibody in an ELISA for final determination of TK activity. This two-step assay is cumbersome to perform with many manual interaction steps and takes excessively long time to execute.

Reliable assays for measuring dCK activity in a sample have not yet been presented.

DEFINITIONS

Figure 1:
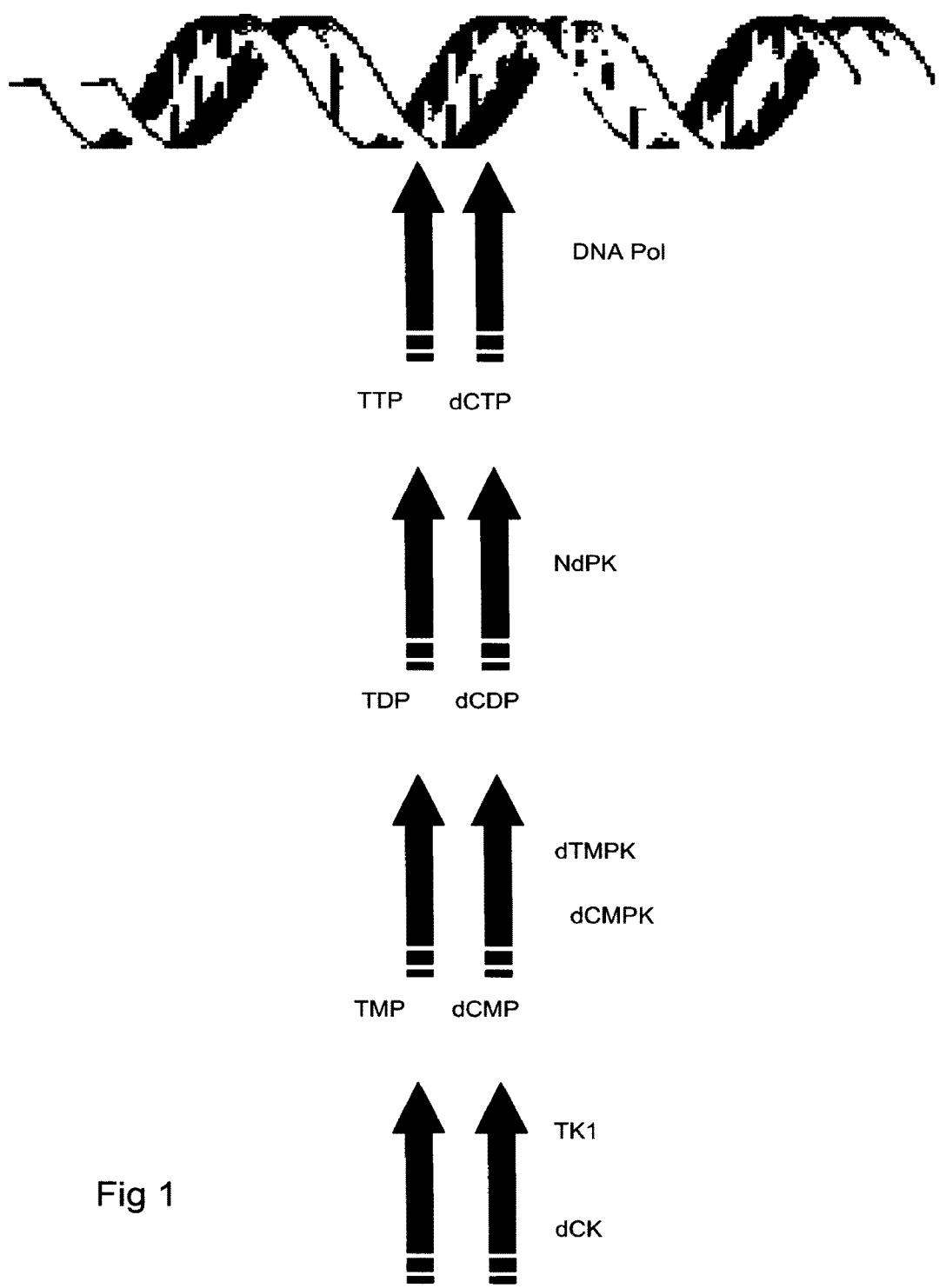
FIG. 1 depicts the salvage pathway for producing TTP and dCTP

All terms and words in the present specification should be construed according to their normal meaning and use in the relevant art. For the sake of clarity, a few terms are more specifically discussed below.

Thymidine and deoxythymidine is used inter changeable during the entire invention, unless otherwise indicated.

Homogenous assay is a non-solid phase assay which generates signal while the primer-template system is being extended, requiring minimal post-primer extension handling. These assays require no separation steps. The reactions occur completely in solution without beads or solid phase attachments to interfere with low affinity interactions. Homogenous assay methods are essential for the throughputs required in drug discovery and for assay miniaturization. In any homogenous assay, all the components of the assay are present during measurement. The elimination of separation steps is the major advantage of these assays, but this presents difficulties because of non-specific measurement of the assay constituents (source: www.genomicglossaries.com, retrieved 28 Apr. 2010.)

Deoxynucleoside is a molecule composed of a nitrogenous base attached to the five-carbon sugar deoxyribose. Deoxynucleosides are often referred to as simply base bound to a deoxyribose sugar. Natural deoxynucleosides are defined as non-modified deoxynucleosides. Examples of these include cytidine, uridine, adenosine, guanosine, thymidine and inosine.

Natural deoxynucleosides are deoxynucleosides in the form present in wild type living organisms, such as humans.

Modified deoxynucleosides, also called nucleoside analogues, are deoxynucleosides with any type of modification on the glycosylamine or the nucleobase. In medicine several nucleoside analogues are used as antiviral or anticancer agents. Examples of modified deoxynucleoside are azidothymidine (AZT), Bromo-deoxyUridine (Br-dU), Iodo-deoxyUridine, Vinyl-deoxythymidine and fluoro-deoxyuridine.

DNA-dependent DNA polymerase is an enzyme that catalyzes the assembly of deoxyribonucleoside triphosphates into deoxyribonucleic acid, with single-stranded DNA serving as the template. In some literature DNA dependent DNA polymerases may also be called DNA-directed DNA polymerase.

A DNA-dependent DNA polymerase may have three distinct enzymatic activities: (a) a 5' to 3' polymerase activity which, under the direction of a template DNA, catalyzes the addition of mononucleotide units, produced from deoxynucleoside 5'-triphosphates, to the 3'-hydroxyl terminus of a primer chain; (b) a 5' to 3' exonuclease active only on duplex DNA; (c) a 3' to 5' exonuclease primarily active on single-stranded DNA which can selectively remove mismatched terminal nucleotides. Note that besides DNA polymerase I, and Taq DNA polymerase and Tth polymerase from *Thermus thermofilus* are the only so far identified DNA-dependent polymerase with 5'→3' exonuclease activity.

DNA template molecule is a ssDNA molecule serving as a template for a DNA dependent DNA polymerase.

DNA primer molecule is a short DNA molecule complementary to a stretch of a DNA template molecule and serves as a primer for the DNA polymerisation by a DNA dependent DNA polymerase.

Intact form: A DNA probe used in the present invention is said to be in its intact form when it is in the form it is in before any polymerase reaction according the invention is performed.

Salvage synthesis pathway is depicted in FIG. 1. is one of the route for synthesis of TTP and dCTP.

TTP and dCTP are triphosphates of the corresponding deoxynucleosides of thymidine and deoxycytidine. These are produced by firstly by transferring a phosphate group from e.g. ATP with help of a deoxyribonucleoside kinase, which will generate the corresponding monophosphate, TMP or dCMP.

dTMP kinase and cytidylate kinase catalyses the formation to the of the corresponding diphosphate nucleoside, TDP and dCDP.

nucleoside-diphosphate kinase converts the di-phosphates to the final triphosphate nucleotides.

RNA-dependent DNA polymerase is the enzyme which catalyses the assembly of deoxyribonucleoside triphosphates into deoxyribonucleic acid, with single-stranded RNA serving as the template during the first strand synthesis.

Abbreviations Used
ATP Adenosine 5'-Triphosphate
AZTMP Azido-thymidine monophosphate
BrdU BromodeoxyUridine
dCDP deoxyCytidine diphosphate
dCK deoxyCytidine kinase EC 2.7.1.21; ATP: cytidine—5'-phopsphotransferase
dCMP deoxyCytidine Monophosphate
dCMPK Cytidylate kinase: EC 2.7.4.14; ATP:dCMP phosphotransferase
dsDNA double-stranded DNA
hrdCK Human recombinant deoxynucleoside kinase
hrTK1 Human recombinant Thymidine kinase 1
MMX MasterMix [reagent mixture without sample]
NdPK Nucleoside-diphosphate kinases: EC 2.7.4.6; ATP: nucleoside-diphosphate phosphotransferase
hrTK1 Human recombinant Thymidine kinase 1
ssDNA single-stranded DNA
TDP deoxyThymidine diphosphate
TK Thymidine kinase: EC 2.7.1.21; ATP: thymidine—5'-phopsphotransferase
TMPK dTMP kinase: EC 2.7.4.9; ATP:TMP phosphotransferase
TMP deoxyThymidine Monophosphate

SUMMARY OF THE INVENTION

The invention aims to provide a general and improved method and kit for detection of deoxyribonucleoside kinase activity(ies). The present inventors have found that there is still a need for an activity based deoxyribonucleoside kinase activity assay kit and method that can detect, not only TK in a sample, but also to testing for dCK e.g. for drug resistance development monitoring during cancer treatment, and which is robust in performance, fast, simple, user-friendly and which is safe for clinical use.

The use of dCK as a diagnostic tool for cancer disease management has not yet found its clinical application. However, several nucleoside analogues, used in cancer treatment such as cytarabine and the newer gemcitabine, are activated by dCK and it is therefore of paramount importance to find efficient solutions for simple determination of resistance development since resistance has been linked to dCK deficiency.

The invention is summarized in the claims.

DETAILED DESCRIPTION OF THE INVENTION

Taq DNA polymerase is a DNA-dependent DNA polymerase from *Thermus aquaticus*. Taq polymerase, or simply Taq, has an optimal temperature interval between 65 to 75° C. The Taq DNA polymerase also incorporates 5' to 3' nuclease activity.

Unexpectedly it was found that the rest-activity of Taq DNA polymerase at 37° C., with respect to both primer extension and 5' to 3' nuclease activity was sufficient enough to release a 5' bound fluorescent marker from a fluorescently dually labelled probe of which one is transferring its energy, quenching, to the other which releases the energy into heat instead of light.

It would thus be possible to measure a deoxyribonucleoside kinase activity in real-time instead of determining the end-point enzyme activity compared to previously presented detection methods for deoxyribonucleoside kinases.

Real-time determination in nucleic acid amplification assay systems has, besides improved sensitivity, the advantages of rapidity, improved resolution, and better precision.

It was also argued that in order for a homogenous deoxyribonucleoside kinase activity assay to be competing with current assays on the market it must be able to measure these activities from healthy volunteers (e.g. from 0.5 U/l to 7 U/l) within 5 h from assay start.

In previous attempts no results were unfortunately, obtained with the primer extension and the 5'-nuclease reaction at 37° C. using the Taq DNA polymerase. Therefore, it was argued and hypothesised, the primer extension reaction and the 5' nuclease reaction of the Taq DNA polymerase could be substituted by the same activities from *Escherichia coli* DNA-dependent DNA polymerase I thus preserving the real-time aspect of a homogenous assay. Disappointingly it turned out that the DNA polymerase I could not be used since this enzyme un-specifically releases the 5' bound fluorophore.

Therefore, it was again argued, the true real-time approach using only one incubation temperature for both reactions must be abandon and replaced with a two-step, temperature shift, procedure, i.e. (1) the TTP or dCTP production had to occur at 37° C., (2) the primer extension coupled 5'-nuclease fluorophore release ha to be incubated at a higher temperature to support the activity of the Taq DNA polymerase e.g. at 51° C. This was expected to work since the Taq DNA polymerase should retain approximately 40% of its highest activity at 51° C.

Furthermore, it was argued, the industrial applicability should be retained since a temperature shift two-step assay can be made invisible for the test provider and the operator by programming the real-time PCR instrument to execute the temperature shift.

Figure 5:
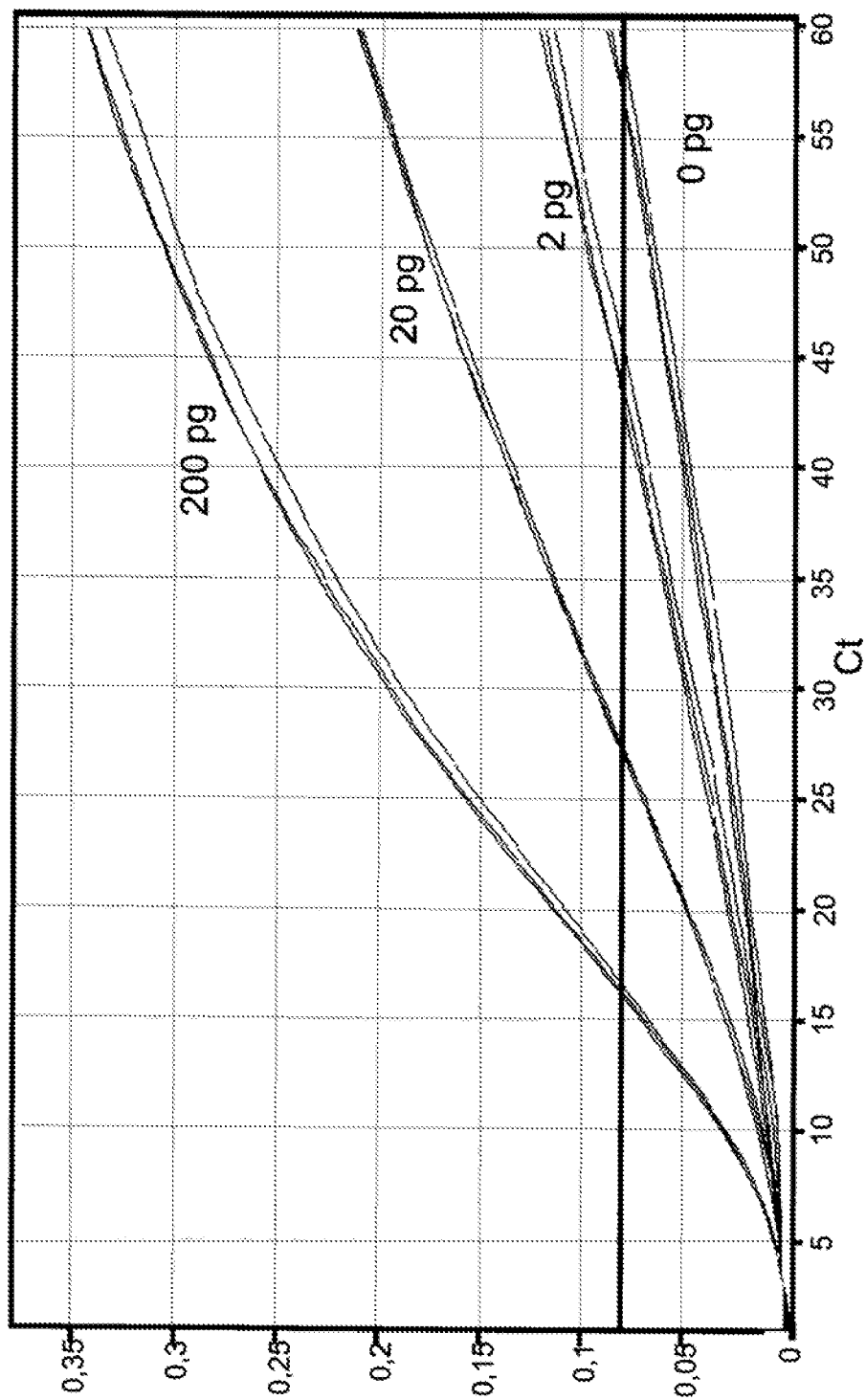
FIG. 5 Fluorescence curves obtained by real-time fluorescence capture reaching threshold level Ct from Example 3 for hrTK1 standard points.
Figure 6:
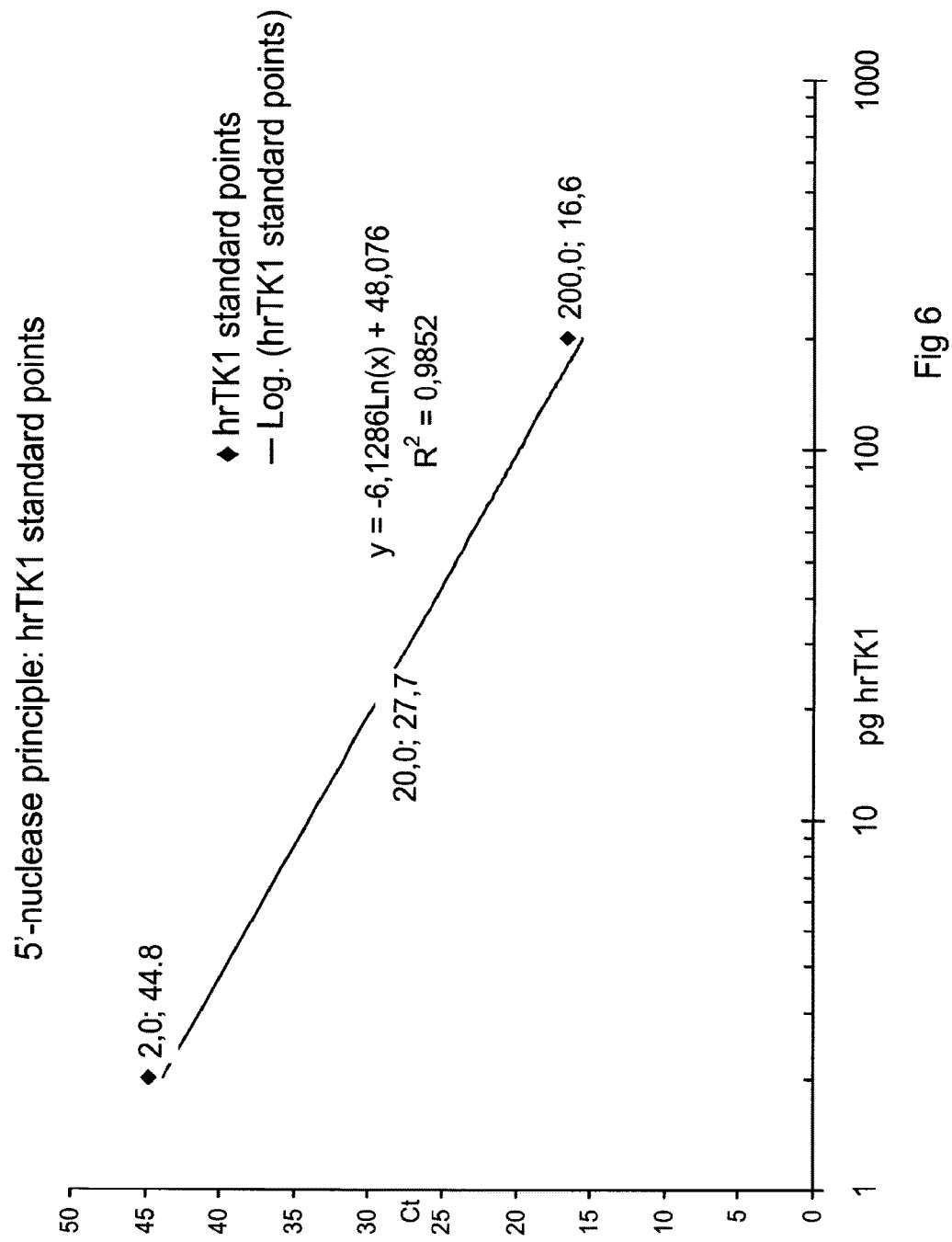
FIG. 6 Linear regression on a logarithmic scale on mean Ct values from Example 3 for hrTK1 standard points.

Therefore and firstly, a primer-template-probe system was constructed to harmonize to the optimal thermodynamic properties for hybridization at 51° C. Taking the $MgCl_2$ concentration into consideration Tm for the probe was calculated to reach 69° C. In the first attempt, measuring only TK activity, surprisingly it turned out that the 37° C. incubation step had produced a fine linear graph of released and normalised fluorescence from two standard points included, i.e. activities from 2000 pg, 200 pg, 20 and 2 pg hrTK1, respectively. An $R^2$ value of 0.9669 was obtained. The linear graph of released and normalised fluorescence from the 51° C. reaction was even worse in to interpret, however still readable. Thus, it was concluded that a possible real-time assay approach for the detection of TK in a sample was at hand. What was even more surprising was the fact that the first experiment indicated the possibility to measure TK activities down to those found in serum samples from normal healthy volunteers within 1 h. This represents an improvement by 4 h from the first preliminary specification. The specific activity of the hrTK1 is estimated to 2.1 μmol/min/mg. The assay only retains the linear and the plateau (saturating) phase descriptive of real-time PCR. The surprising effect of real-time detection of TK activity at 37° C. immediately solved two other problems connected with a two-step temperature shift procedure. First, TK displays characteristic TTP inhibition. This could render the two-step assay difficult to perform for high TK activity containing samples, i.e. a dilution step would be required. Now this can be omitted since the TTP or dCTP produced is constantly being removed by the Taq DNA polymerase through the incorporation of TTP or dCTP into the primer-template system(s). Secondly, the very high polymerising rate of Taq DNA polymerase (35-100 nt per s at 72° C.) at higher temperature, such as 51° C. may cause some sever problems interpreting the assay results in real-time since higher TK activity values, even from as low as 10 U/l, will develop within minutes from start of the assay and thus severely hamper the resolution. At the same time activities from healthy volunteers may require hours before a signal can be detected due to the fact that resolution of signals requires that only a limited amount of Taq DNA polymerase U per reaction can be used. In summery; a non-evident finding was disclosed which can now be turned into an industrial applicable assay and method for the detection of deoxyribonucleoside kinase activities, FIG. 5. The sensitivity of the assay was verified in the subsequent experiment, example 3.

In summary it has now been found that the natural substrate thymidine (T) and/or deoxycytidine (dC), or a mix thereof, and a DNA-dependent DNA polymerase are essential reagents needed for measuring deoxyribonucleoside kinases catalytic concentration(s) such as TK or dCK. This can be done in a homogenous mix with other known components for a TK or dCK activity assay. The assay is made robust in performance, rapid and simple to perform and clinically safe by coupling complementation of TK or dCK catalytic activity, in a sample, with activities from other nucleoside kinases such as dTMP kinase, or cytidylate kinase, and nucleoside-diphosphate kinase present in a reaction mix. These reagents can conveniently be included in a kit and in a buffer for the production of TTP, or dCTP, with primer extension using a primer-template-detector system, each with fixed concentrations. The reagents in the reaction mix without sample will, in the rest of this document, be referred to as the master mix, abbreviated MMX. A DNA-dependent DNA polymerase may also be included in the MMX. Table 1 summarizes current prior art situation with respect to kit components incorporating a method for the determination of deoxyribonucleoside kinases. In summery none of the previous deoxyribonucleoside kinase kit claims incorporates a DNA-dependent DNA polymerase and a natural T and/or dC substrate, or a mixture thereof, or a method using the same.

TABLE 1

Prior art kit components compared to the invention

| Reagent | Kit claims | | | |
|---|---|---|---|---|
| | US2008248472 | EP1385005 | WO2009/063254 | Present invention |
| RNA-dependent DNA polymerase | + | − | − | − |
| DNA-dependent DNA polymerase | − | − | − | + |
| dT | − | − | − | + |
| dC (together with or replacing dT) | − | − | − | + |
| dU (Br, I) | + | + | + | − |
| Azidothymidine | − | + | − | − |
| Primer | + | − | − | + |
| Direct NA based detection Tool | − | − | − | + |
| Template | + | − | − | + |
| Thymidylate kinas | + | − | − | + |
| Nucleoside di-phosphate kinase | + | − | − | + |
| Buffer | + | + | + | + |

Homogenous PCR assays for detection and measurement of nucleic acid target in a sample, such as from bacteria and viruses, have become an extremely important assay method in clinical diagnostics.

Different detecting technologies have been applied to homogenous PCR assays. These include quenching technologies using intercalating molecular detectors, and quenching probe technologies such as dually labelled FRET nucleic acid probes and the so called molecular beacon method which utilizes contact quenching nucleic acid probes.

The practice of the invention employs well known techniques in molecular biology and enzymology which are within the skills of the art. According to the invention a kit comprising a DNA-dependent DNA polymerase and natural T or dC as substrate can be used in combination with several detection moieties to measure in a sample the catalytic concentrations of TK or dCK.

The kit may also be completed with a phosphotransferases such as TMPK or dCMPK and the NdPK. These components can conveniently be derived from a non-recombinant natural host or from recombinant enzyme expressed from eukaryotic or bacterial vector systems carrying the active gene of the complementing enzyme.

Design of the Primer-template-probe Detector System

In all preferred aspects of the invention it is important to design the primer-template-probe system. The choice of DNA-dependant DNA polymerase has to match the choice of the primer-template-detector.

The present invention does not require temperature cycling shifts, as with the case of real-time PCR. However, using a dual labelled single stranded and FRET quenched DNA probe as a detector, FIG. 2, the detection is easily done in real-time. The primer-template-probe system is here designed to direct the probe to hybridize before the primer to the template by constructing the probe sequence to attain a 3-15° C. higher Tm than the primer thus preferentially binding faster than the primer to the template. Even more preferred is 5-10° C. higher Tm. Most preferred is 7-9° C. higher Tm. Next the pre-requisite for a TTP or dCTP to initiate the primer extension may impose a short delay in order for the probe to preferentially bind to the template before the primer. With this detector system, FIG. 2, Taq DNA polymerase is the most preferred DNA-dependent DNA polymerase of the invention. The concentration of Taq DNA polymerase may range from 0.01-4 U per reaction. More preferred is 0.1-2 U per reaction. Even more preferred is 0.3-1 U of Taq DNA polymerase per reaction. Most preferred is 0.5 U per reaction of Taq polymerase. The design of the primer has to take the Förster radius between the quencher and the 5'-fluorphor using the 5' nuclease assay in consideration.

Figure 3:
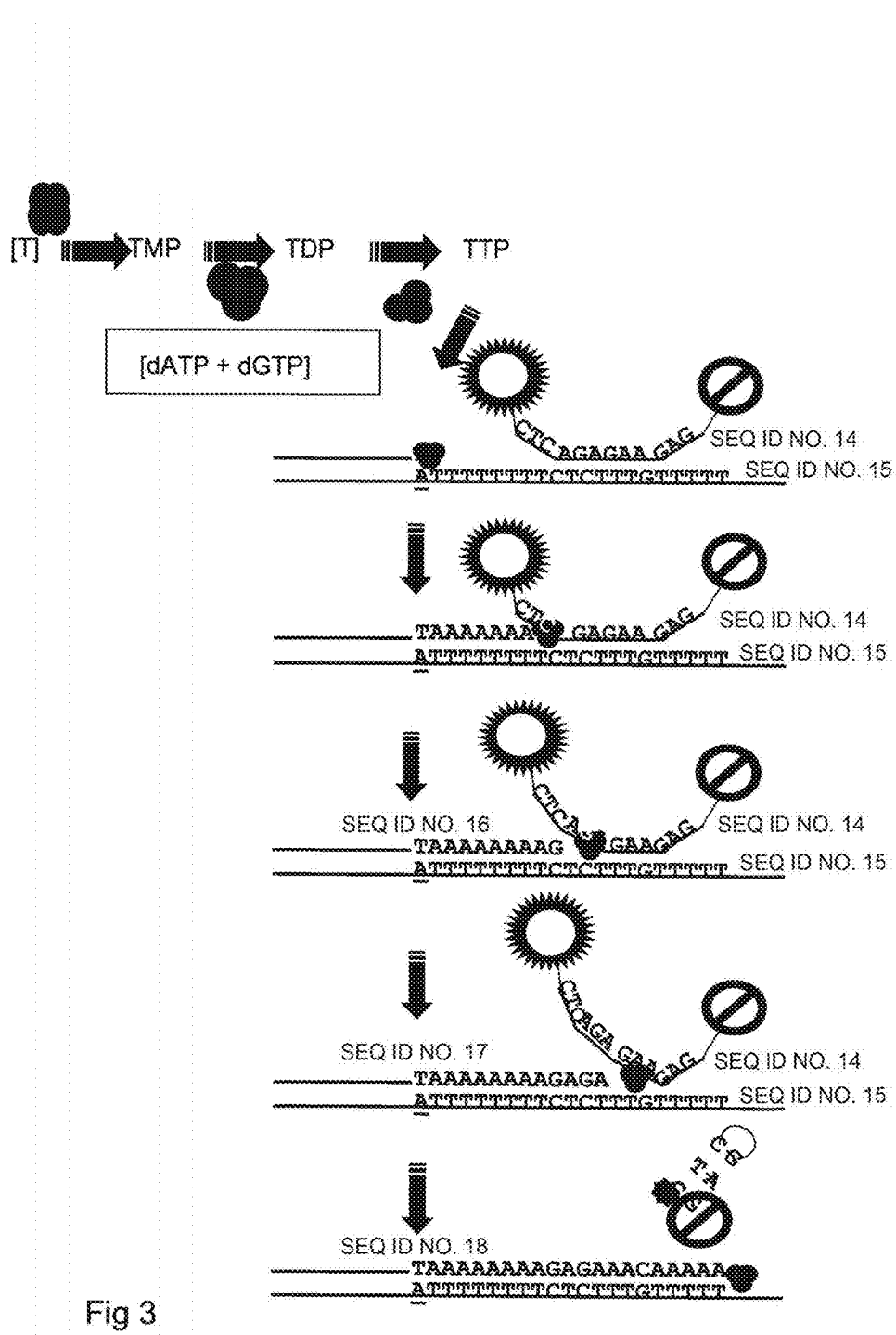
FIG. 3 depicts the principle of detection system 3 of the method according to the invention. SEQ ID NOs.: 14-18 are shown.

Using as detector a fluorescently dual labelled single stranded DNA probe which in its intact and non-hybridized form is quenched, such as an molecular beacon probe, FIG. 3, imposes the same temperature strategy for the hybridisation step. The primer-template-probe system is designed to direct the probe to hybridize before the primer to the template by constructing the probe sequence to attain a 3-15° C. higher Tm than the primer thus preferentially binding faster than the primer to the template. Even more preferred is 5-10° C. higher Tm. Most preferred is 7-9° C. higher Tm. Next the pre-requisite for a TTP or dCTP to initiate the primer extension may impose a short delay in order for the probe to preferentially bind to the template before the primer. To carry out the detection according to the invention as described in FIG. 3, the DNA-dependent DNA polymerase has to carry a DNA strand displacement activity. With regards to this detector system of the invention the concentration of displacing DNA polymerase may range from 0.01-5 U per reaction with respect to DNA polymerase used. More preferred is 0.1-3 U per reaction.

Figure 4:
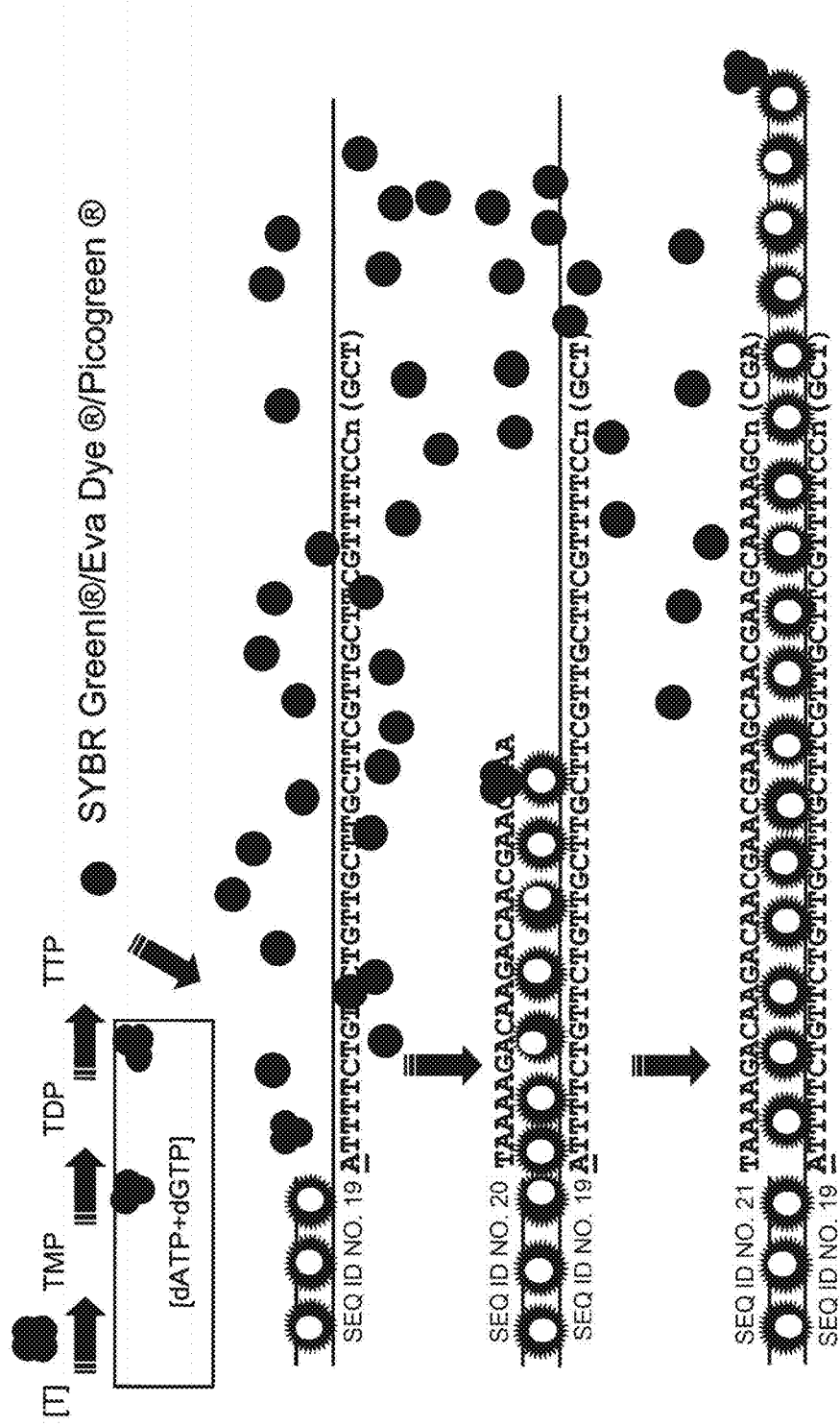
FIG. 4 depicts the principle of detection system 1 of the method according to the invention. SEQ ID NOs.: 19-21 are shown.

With regards to the last detector system, FIG. 4, double stranded DNA generated through by primer extension, allows for the binding of a surface binding or intercalating fluorescent molecule, to be detected upon binding, FIG. 4. The DNA polymerase used for this detection system might preferably be a 3'→5' exo⁻ DNA-dependant DNA polymerase exemplified with Klenow exo⁻ DNA polymerase. The concentration of the DNA polymerase may range from 0.01-4 U per reaction depending on enzyme preferred. More preferred is 0.1-2 U per reaction.

Detection of Signals from Different Detector Systems

The instrument for signal detection can preferentially be a real-time PCR instrument. No preference with respect to the heating-cooling principle or exiting and light emitting detection principle of the instrument applies to the method according to the invention.

The method according to the invention can use $C_t$ values which are subsequently converted to the catalytic concentration definitions such as Unit enzyme activity per liter (U/l). It should be understood that the method according to the invention can chose between Ct value and time-unit during the signal sampling. The method uses agreed definitions for catalytic concentration.

The amount of TK or dCK in the sample is preferably determined by any of the detection methods by correlating the cycle number, at which the sum of the fluorescence increase or decrease, depending on detection system used, reaches a threshold detectable level.

Kit Design

The DNA-dependent DNA polymerase and the natural T or dC substrate may be dispensed into one or a plurality of reaction containers.

Reaction container suitable for carrying out the method according to the invention in a fluorescent detection instrument is preferably capable to keep a total volume of 20 µl's to 200 µl's. Even more preferred the reaction container is capable to keep a volume of 25 µl or 50 µl. The reaction volume of the method according to the invention can preferably range from 5 µl to 100 µl. Even more preferred reaction volume is 25 µl to 50 µl.

Sample Handling Using the Kit

Subsequent to having added the MMX to the reaction container the sample is added to the container. The container is closed and put into the measuring instrument and incubated. Fluorescent sampling commences and continues for the selected number cycles. The TK/dCK sample can preferably constitute serum or plasma. Even more preferred is serum and citrate plasma. The proportion of sample of the reaction volume shall preferably be between 1-20%.

The method according to the invention couples production of TTP or dCTP with primer extension and fluorescent signal development for the detection and determination of catalytic concentration of TK or dCK in a sample. Briefly, TTP or dCTP is produced by TK or dCK, from the sample, together with the complementing activities of TMPK, or dCMPK, and NdPK comprising the kit. TMPK, or dCMPK, and NdPK are preferably present in the reaction in excess to the highest suspected concentration of TK or dCK in a sample, e.g. >3000 U/l. With respect to NdPK, from 1× to 1000× the catalytic concentration represented by 2000 pg hrTK1 (ca. 10000 U/l). Even more preferred is a concentration of NdPK that is between 50× to 1000× the catalytic concentration represented by 2000 pg of hrTK1. With respect to TMPK, or dCMPK, from 1×-1000× the catalytic concentration represented by 2000 pg of TK is preferred. Even more preferred is a concentration that is between 5× to 100× the catalytic concentration represented by 2000 pg of hrTK1.

TTP or dCTP substrate is continuously utilized by the DNA-dependent DNA polymerase, conveniently comprising the kit, to execute the primer extension reaction according to any of the three detection system to create a fluorescent signal which can subsequently be correlated to the TK or dCK catalytic concentration in the sample. It is a preferred, for all three detection system, that the template has one or a plurality of "A"s or a "G"s in the template nucleotide sequence downstream of the primer binding complementary sequence, i.e. in the 5'-direction of the template sequence, depending on what the deoxyribonucleoside kinase which is to be measured. In case of detecting deoxyguanosin kinase (dGk) the template needs one or a plurality of "C"s downstream of the primer. For the reason of clarification it is herby noted that each primer-probe-detector set, irrespective of detection system used, is at least specific with regards to template and the deoxyribonucleoside kinase this is intended to detect. Multiplex detection, i.e. detection of a plurality of deoxyribonucleoside kinases in the same reaction container, using the 5' nuclease detection system also requires specific probe sequences and labels.

Figure 2:
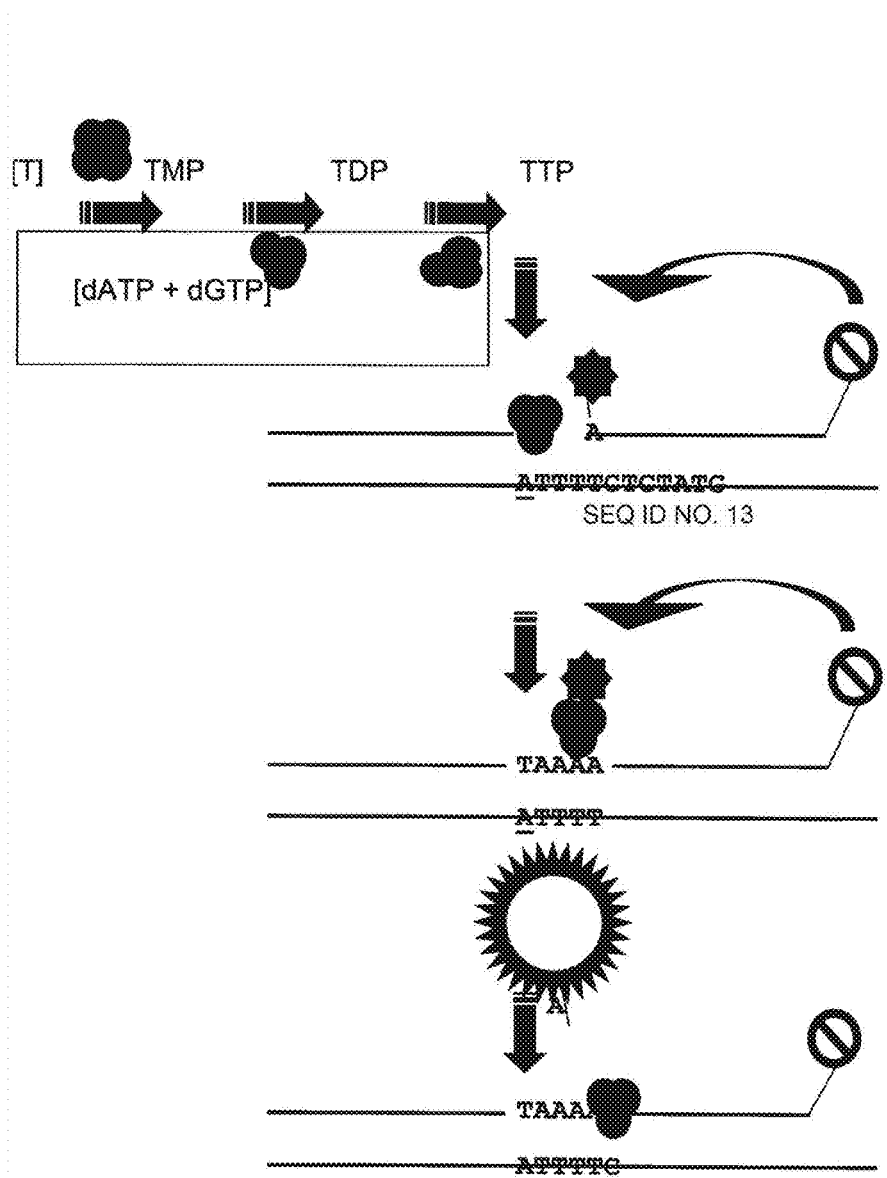
FIG. 2 depicts the principle of detection system 2 of the method according to the invention. SEQ ID NO.: 13 is shown.

In one of the detection systems, FIG. 2, also referred to as detection system 1, the fluorescence from a single stranded oligonucleotide probe having a 5'-covalently bound fluorophor and a quencher fluorophor covalently bound to the same probe in the 3'-direction, is quenched by the action of dynamic quenching or FRET. During the course of the primer extension reaction, using pre-determined amounts of primer, template and probe, the 5'-covalently bound fluorophor is released, i.e. hydrolyzed away from the probe by the 5'→3' exonuclease activity of the DNA-directed DNA polymerase.

In another detection system, also referred to as detection system 2, FIG. 4, the fluorescence from intercalating or surface binding fluorogenic molecules exemplified but not limited to SYBR Green I®, Picogreen® and Eva Green Dye®, is quenched, in its free or unbound state. During the course of the primer extension reaction which uses pre-determined amounts of template and one primer fluorogenic molecules are intercalated or surface bound to the double stranded DNA produced at which it start to fluoresce.

In a third detection system, also referred to as detection system 3, FIG. 3, the fluorescence from a single stranded oligonucleotide probe comprising a so called molecular beacon having a 5'-covalently bound fluorophor, a quencher fluorophore covalently bound to the same probe 3'-distal to the 5'-bound fluorophore which is quenched by the action of contact quenching or static quenching.

Prior to the onset of the incubation and real-time cycling the molecular beacon probe is denatured and allowed to hybridize to the target template. When hybridised to the template the contact quenching is released and maximum fluorescence is reached at time zero. During the course of the primer extension, using pre-determined amounts of primer, template and probe, the probe is displaced by the action of the Φ29 DNA polymerase or the Bsm large fragment DNA polymerase or the Bst Large Fragment DNA Polymerase. The two latter DNA polyermases are lacking the 3' →5' exonuclease activity. When the molecular beacon is displaced it retains it stem-loop structure form and contact quenching turns out the fluorescence in relation to the TTP or dCTP production per unit time. Using Dabcyl absorbs the fluorescence from the 5' fluorphor. In all 3 detection systems detection is done in real-time A kit related to the detection system 1 may comprise a DNA-dependent DNA polymerase and a natural T or dC substrate, or Br-dU or dC, most preferably a natural T or dC substrate. Preferably the DNA-dependent DNA polymerase is devoid of 3'→5' exonuclease.

Preferably the kit includes the TMPK, or dCMPK, to a concentration of 0.001→100 ng/reaction, even more preferably 0.01→10 ng; 0.02-0.002 U/L NdPK/reaction; a γ-phosphate donor such as ATP, UTP, CTP or GTP between 0.5-15 mM, more preferably 3-6 mM most preferred 4-5 mM ATP.

A primer, 10-20 nucleotides long, more preferred 10-15 nucleotides long. The primer may be minor groove binding modified primer. Example of primer is SEQ ID: 9

A template, 50-1000 nucleotides, more preferably 75-250 nucleotides, having a 3'-proximal sequence complementary to the primer sequence; preferably the template sequence has, for the detection of TK or dCK, one or a plurality of "A"s or "G"s 1-10 nucleotides downstream of the primer binding site i.e. in the template 5'-direction, even more preferred, at the position immediately downstream of the 3'-end of the complement to the primer sequence. Most preferred one A, or one G, is positioned at the position immediately downstream of the 3'-end of the complement to the primer sequence. The nucleotide composition forming the rest of the template sequence is preferably a mixture of T's, C's and G's, for the detection of TK activity, or A's in place of G, for the detection of dCK activity, at a preferred ratio of 60-40% GC. Example of templates is SEQ ID: 7

An intercalating or surface binding fluorogenic molecule exemplified by e.g. SYBR GreenI®, Picogreen®, or Eva Green Dye®.

Furthermore the kit may include deoxynucleotide triphosphates, dGTP, dATP, TTP and dCTP.

The kit may include enzyme stabilizing reagents such as DTT or DTE, to a final concentration between 2-8 mM; BSA to a final concentration between 0.2-1% (W/V); $Mg^{2+}$ as $MgCl_2$, to a concentration of 5 mM to 12 mM; most preferably 5-10 mM.

The DNA-dependent DNA polymerase is preferably at a concentration between 0.01-5 U/reaction. The natural T or dC substrate is preferably between 0.01 mM-1 mM even more preferably 0.1 mM.

In a method related to a detection system utilising an intercalating molecule the mixture of the MMX and the sample, is preferably incubated, at 36-42° C. or even more preferred at 37° C. for 30-220 min and determining the amount TK, or dCK, in a sample in real-time by correlating the number of fluorescence capturing cycles (Ct's) needed for the normalized fluorescence to cross a selected threshold level of fluorescence. Next fitting the threshold Ct crossing point to Ct's for pre-selected samples of a known number of different TK U/l, or dCK U/l, constituting standard curve, FIG. 7, for respective deoxyribonucleoside kinase. Values are extrapolated to a standard curves consisting of two to eight different catalytic concentrations of either TK or dCK, preferably any concentration between 1-3 U/l; 10-20 U/l and 50-100 U/l, 100-500 U/l and 500-1500 U/l. The standard curves comprising the differently assigned TK, or dCK.

A kit for the detection of TK or dCK using the detection system 2 may comprise a DNA-dependent DNA polymerase and a natural T, or dC, substrate, or BrdU or dC. Most preferred is a natural T, or dC, substrate. Preferably the DNA-dependent DNA polymerase is devoid of 3' →5' exonuclease, but has a 5'→3' exonuclease activity such as e.g. Taq DNA polymerase or Tth DNA polymerase.

Preferably the kit includes TMPK or dCMPK to a concentration of 0.001-100 ng/reaction, even more preferably 0.01-10 ng; 0.02-0.002 U/L NdPK. A γ-phosphate donor is required, such as ATP, UTP, CTP or GTP, at a concentration between 0.5-15 mM, more preferably between and 4-6 mM. Most preferred 5 mM ATP.

A primer, 10 to 20 nucleotides long, may be included in the kit. Primers are exemplified of in SEQ ID: 2 and SEQ ID: 5. Most preferred the primer is 10-15 nucleotides long.

The primer may be a minor groove binding modified primer.

A template for use in detection system 2 may be included in the kit with a length of 25-200 nucleotides. Examples of the templates are shown in SEQ ID: 1 and SEQ ID: 4. The template comprises a 3'-sequence complementary to the primer and a downstream, i.e. towards the template 5' end, a sequence complementary to the dually labelled nucleic acid probe. The template sequence may comprise one or a plurality of "A"s, or "G"s, positioned 1-10 nucleotides downstream from the 3'-end of the primer, even more preferably immediately downstream from the 3'-end of the primer. The nucleotide composition forming the rest of the template sequence is preferably a mixture of T's, C's, G's and A's at a preferred ratio of 60-40% GC. A probe, 10 to 30 nucleotides long, exemplified with SEQ ID: 3 or SEQ ID: 6, which is covalently labelled with a fluorophor and quencher pair known in the art to be functionally compatible. For example for a TK specific template the 5' bound fluorophor of the probe may comprise a 6-FAM fluorophor label and the 3'-distal nucleotide may carry a BHQ1 quenching fluorophor label (Biosearch Technologies Inc.). For a dCK specific template the probe may carry a TET fluorophor label in place of 6-FAM together with BHQ1 bound to the 3'-distal nucleotide. The spectral difference between 6-FAM and TET is great enough (11 nm) to make it possible to distinguish between the light emitted from the two fluorophors even when running in a multiplex format. The nucleotides TTP, dCTP, dGTP and dATP may be included in the kit. The kit may include an enzyme stabilizing reagents such as DTT or DTE, to a final concentration between 2-10 mM; BSA to a final concentration between 0.2-1% (W/V); monovalent cations as salt e.g $K^-$ as KCl, to concentration between 40-100 mM, most preferably 50 mM; divalent cations e.g. Mg2+ as $MgCl_2$ or $MgSO_4$, to a concentration of 5 mM to 14 mM; most preferably 7-12 mM. The DNA-dependent DNA polymerase is preferably present at a concentration between 0.01-2 U per reaction. The T or BrdU or dC substrate or the natural T or dC substrate is preferably present at a concentration between 0.01 mM-1 mM even more preferably 0.1 mM.

A method described in FIG. 2 using these kit components comprises incubating the sample and MMX preferably at 33° C. to 42° C. even more preferably at 37° C. for 30-200 minutes and in real-time and continuously capture and measure the increase in signal from the detector. Determine the amount TK or dCK in a sample preferably by correlating the number of fluorescence capturing cycles (Ct's) needed for the normalized fluorescence (i.e. the remaining fluorescence from a sample after the background fluorescence has been deducted from the total fluorescence, at least, over the first five capturing cycles after start of fluorescence capturing) to cross a selected threshold level, or by correlating to the time needed to reach the same threshold. Fitting the threshold Ct of the sample to a standard curve constructed from preselected standards of known catalytic concentrations of TK or dCK expressed in U/l. Determination of the threshold level can be done either prior to the run, by setting a fix threshold, or after the run has completed by setting the threshold level for the lowest included deoxyribonucleoside kinase activity control e.g. the negative control containing 0 U/l crossing at the last minute of the run.

A kit for the detection of TK or dCK using the detection system 3, depicted in FIG. 3, may comprise a DNA-dependent DNA polymerase and the natural substrate T or dC or BrdU or dC, most preferably T or dC natural substrates. Preferably the DNA-dependent DNA polymerase is a displacing active polymerase such as exemplified with Φ29 DNA polymerase or the large fragment of the Bsm DNA polymerase from *Bacillus smithii* (K.K. DNAFORM) or Bst DNA Polymerase Large Fragment from *Bacillus stearothermophilus* (New England Biolabs Inc.).

Preferably the kit includes TMPK or dCMPK to a concentration of 0.001-100 ng/reaction, even more preferably 0.01-10 ng; 0.02-0.002 U/L NdPK. A γ-phosphate donor is required, such as ATP, UTP, CTP or GTP, at a concentration between 2-8 mM, more preferably between and 4-6 mM. Most preferred is a concentration of 4 mM ATP.

A primer, 7 to 20 nucleotides long, may be included in the kit. Example of the primer is shown in SEQ ID: 9. The primer sequence may be a minor groove binding primer. Most preferred the primer is 10-16 nucleotides long.

A template may be included in the kit with a length of 30-1000 nucleotides. Example of template sequence are shown in SEQ ID:8. The template comprises a 3'-sequence complementary to the primer and a downstream, i.e. towards the template 5' end, a sequence complementary to the dually labelled nucleic acid probe. The template sequence may comprise one or a plurality of "A"'s, or a "G"'s, positioned 1-10, more preferred is that the nucleotides are between 2-4 nucleotides downstream from the 3'-end of the primer, even more preferably immediately downstream from the 3'-end of the primer. The nucleotide composition forming the rest of the template sequence is preferably a mixture of T's, C's, G's and A's at a preferred ratio of 60-40% GC. The kit may contain a molecular beacon probe. The structure of the probe is exemplified in FIG. 3. The probe may comprise a 5' covalently bound fluorophore and quencher fluorophore towards the 3'-end. Preferably the quencher is contact quencher fluorophore such as Dabcyl and functions according to the contact quenching principle. Examples of probe sequences are shown in SEQ ID:10. The nucleotide composition forming the rest of the template sequence is preferably a mixture of T's, C's and G's or A's at a preferred ratio of 60-40% GC.

Other components of the kit may be TTP, dCTP, dGTP, dATP or other modified nucleotides; enzyme stabilizing reagents such as DTT or DTE, to a final concentration between 2-8 mM; BSA to a final concentration between 0.2-1% (W/V); monovalent cations as salt e.g. K— as KCl, to concentration between 5-100 mM, most preferably 10 mM; divalent cations e.g. $Mg^{2+}$ as $MgCl^2$, to a concentration of 5 mM to 12 mM; most preferably 5-10 mM.

The kit may contain a DNA polymerase having DNA strand displacement characteristics exemplified with large fragment of the Bsm DNA polymerase DNA polymerase. Even more preferred is a DNA dependant DNA polymerase having strand displacement characteristics and devoid of 3'→5' exonuclease activity. The displacing DNA-dependent DNA polymerase is preferably at a concentration between 0.01-2 U/reaction. The T or BrdU or dC substrate or the natural T or dC substrate is preferably between 0.01 mM-1 mM even more preferably 0.1 mM.

A method described in FIG. 3 using these kit components comprises incubating the sample and MMX preferably at 33° C. to 42° C. even more preferably at 37° C. and in n real-time continuously measure the decrease in fluorescence. Determine the amount TK or dCK in a sample preferably by correlating the number of fluorescence capturing cycles (Ct's) needed for the normalized fluorescence (i.e. the remaining fluorescence from a sample after the background fluorescence has been deducted from the total fluorescence, at least, over the first five to 18 cycles after start) to cross a selected threshold level, or by correlating the time needed to reach the same threshold. Fitting the threshold Ct of the sample to a standard curve constructed from pre-selected standards of known catalytic concentrations of TK or dCK expressed in U/l.

In WO10036359 a kit is described for assays of polymerase activities. The method and kit in WO10036359 does not discuss how polymerase activities can be detected in a sample with serum. There is a need for a kit that can detect polymerase activity in samples with serum.

EXAMPLES

The following applies to all detection systems described in this section of the document.

Reaction tubes and PCR instrument are the same for all examples following Example 1.

Buffer mix is the same as for all examples following Example 1.

MMX is defined to comprise all components except the deoxyribonucleoside kinase containing sample to be tested including negative control in which the deoxyribonucleoside kinase sample has been replaced with buffer Sample can be either recombinant or purified deoxyribonucleoside kinase or serum or plasma comprising the same.

Dilution of deoxyribonucleoside kinases is for all examples done in the buffer described in Table 2.

Reaction volume irrespective of detection system is 25 μl.

All samples are run in triplicates irrespective of detection system used.

Example 1 hrTK1 Standard Curve According to Detection System 1

A standard curve was constructed representing hrTK1 catalytic activity values from 200 pg, 20 pg and 2 pg of hrTK1. A 0 pg standard point was included as a hrTK1 negative control and for determination of the threshold level of normalised fluorescence. Specific activity of the hrTK1 was 2.1 μmol $min^{-1}$ $mg^{-1}$. Each standard point was run in triplicates. hrTK1 was diluted in TK dilution buffer, Table 2.

TABLE 2

| TK dilution buffer. | |
|---|---|
| Reagens | Final koncentration |
| Tris-HCLpH 7.6 | 5.00E−02M |
| BSA | 0.50% |
| Triton X-100 | 0.1% |
| DTT | 5.00E−03M |

Briefly, enzyme mixes were prepared to contain each standard point of hrTK1 together with: NdPK from yeast diluted 500× giving a final catalytic concentration of 0.01 Unit per reaction and TMPK, diluted 50× equal to 36 ng per reaction. Specific activity for the yeast NdPK and recombinant TMPK is estimated to 5.4 and 3 μmol/min/mg respectively. Buffer-, substrate- and oligonucleotide mixes were prepared according to Table 4. A 3.2*25 μl MMX for each standard point was prepared at room temperature in a 1.5 ml polypropylene micro centrifuge tube (including the 0 pg hrTK1 negative control) by mixing: buffer-, substrate-, and oligonucleotide mixes (Table 3) together with 0.8 U of Klenow exo⁻ DNA polymerase.

TABLE 3

MMX and enzyme mix for TK determination according to detection system 1.

| Reagent | Assay concentration | mix | Comments |
|---|---|---|---|
| deionised water | — | — | |
| Buffer: Tris-HCl pH 8.0 (25° C.) | 50 mM | Buffer mix | Ambion. 1M stock, AM9855G |
| MgCl$_2$ | 5.0 mM | Buffer mix | Ambion. 1M stock, AM9530G Sigma-Aldrich AG, A-6003. |
| BSA | 0.5% | Buffer mix | 10% stock solution. Heat inactivated @ 56° C. 20'. |
| DTT | 8.0 mM | Buffer mix | Sigma-Aldrich AG |
| deoxyThymidine (T) | 100 μM | Substrate mix | Sigma-Aldrich AG, 89270 |
| deoxyCytidine (dC) | 100 μM | Substrate mix | Sigma-Aldrich AG, D3897 |
| SYBR GreenI | 100 μM | Substrate mix | InVitrogen Inc.. Stock 0.1M |
| dATP | 100 μM | Substrate mix | Fermentas UAB. Stock 0.1M R0181 |
| dGTP | 100 μM | Substrate mix | Fermentas UAB. Stock 0.1M R0181 |
| dCTP | 100 μM | Substrate mix | Fermentas UAB. Stock 0.1M R0181 |
| Phosphate group donor ATP | 4.0 mM | Substrate mix | Supplied by Uppsala University Dept. of Medical Sciences |
| SEQ ID: 9 Primer O33XTMB | 300 nM | Oligonucleotide mix | Delivered by Cybergene AB, Sweden. |
| SEQ ID: 7 Template O31TTSG | 600 nM | Oligonucleotide mix | Delivered by Cybergene AB, Sweden. |
| Klenow exo$^-$ fragment | 0.8 U per reaction | | Fermentas AB, EP0422 |
| Recombinant bacterial TMPK | 36 ng per reaction | Enzyme mix | Original cDNA cloned into pET14b. Protein expressed and purified from *E. coli* host BL21-(DE3) pLys. Provided by Dr. Liya Wang |
| NdPK | 0.01 U per reaction | Enzyme mix | From Sigma Aldrich AG N0379 purified from bakers yeast. hrTK1, Met-106 variant. |
| Recombinant human TK | 2 pg; 20 pg; 200 pg | Enzyme mix | Original human cDNA cloned into pPET14b vector to yield pETKW3. Protein expressed and purified from *E. coli* host BL21-(DE3) pLys. Provided by Dr. Liya Wang, Swedish University of Agricultural Sciences, department of Anatomy, Biochemistry and Physiology. |

The 200 pg enzyme mix of was included in the No-Template-Control MMX. 25 μl was dispensed into 100 μl PCR tubes (Qiagen GmbH) in triplicates. Tubes were closed and placed into a Rotor-Gene Q 3000 (Qiagen GmbH) real-time PCR instrument. Run profile was: (1) Hold at 42° C. for 2 min, (2) Hold at 35° C. for 1 min, (3) Hold at 37° C. for 15 min (4) Cycling: 37° C. for 30 s→37° C. 30 s with signal acquisition to the SYBR Greene/FAM channel (excitation at 470 nm detection at 510 nm). Each cycle was repeated 90 times. Total assay time is 108 min.

Results.

Normalisation of fluorescence is made from cycle 1. Threshold was selected for 0 pg of hrTK1 crossing after 90 cycles (minutes). In this example a threshold at 0.000 normative fluorescence units was obtained. On the X-axis are given the activity from respective standard point given as pg of deoxyribonucleoside kinase. Each standard point carries the pg(X);Ct(y) value. An $R^2$ value of 0.965 is obtained indicating that the standard curve can serve as tool for determining the amount of TK U/1 in a sample.

Example 2 dCK Standard Curve from hrdCK According to Detection System 1

A standard curve was constructed representing hrdCK catalytic activity values from 20000 pg; 2000 pg, 200 pg, 20 pg and 2 pg of enzyme. A 0 pg standard point was included as a hrdCK negative control and for determination of threshold level for normalised fluorescence. Briefly, enzyme mixes were prepared to contain each standard point of hrTK1; NdPK as in Example 1 and dCMPK diluted 50×, equal to 48 ng of enzyme per reaction (Table 4). Specific activity of recombinant dCMPK is estimated to 35 µmol/min/mg. A 3.2*25 µl MMX was prepared for each standard point at room temperature in a 1.5 ml polypropylene micro centrifuge (including the 0 pg hrdCK negative control) by mixing buffer-, substrate- and oligonucleotide mix's together with 0.8 U of Klenow exo⁻ fragment DNA polymerase. MMX preparation was the same as for Example 1 except that dCTP is replaced by TTP in the MMX. Oligonucleotide mix is according to Table 4.

TABLE 4

Oligonucleotides and enzyme mixes for measurement of hrdCK catalytic concentration according to FIG. 4 and different from example 1.

| Reagent | Assay concentration | mix | Comments |
| --- | --- | --- | --- |
| Substrate: TTP | 100 µM | Substrate mix | Fermentas AB. Stock 0.1M R0181 |
| SEQ ID: 9 Primer O33XTMB | 300 nM | Oligo-nucleotide mix | Delivered by Cybergene AB, Sweden. |
| SEQ ID: 12 Template O9TCSG | 600 nM | Oligo-nucleotide mix | Delivered by Cybergene AB, Sweden. |
| Recombinant dCMPK | 48 ng per reaction | Enzyme mix | Provided by Dr. Liya Wang. |
| Recombinant dCK | 20 pg; 200 pg; 2000 pg and 20000 pg | Enzyme mix | hrdCK. Original human cDNA cloned into pET-9d containing a 6xHis tag an a thrombin cleavage site. Provided by Dr. Liya Wang. |

Finally the enzyme mix from respective standard point was added. The 2000 pg enzyme mix of hrdCK was included in the NTC MMX. Next, 25 µl was dispensed into three separate PCR tubes.

Tubes were closed and placed into the real-time PCR instrument. Cycling profile was: (1) Hold at 42° C. for 2 min, (2) Hold at 35° C. for 1 min, (3) Hold at 37° C. for 15 min (4) Cycling: 37° C. for 30 s→37° C. 30 s with signal acquisition to the SYBR GreenI®/FAM channel (excitation at 470 nm detection at 510 nm). Each cycle was repeated 90 times. Total assay time 108 min.

Results Fluorescence normalisation is from cycle 1. Threshold selected for 0 pg after 90 min. Threshold was set at 0.017 normative fluorescence units. On the X-axis are given the activity from respective standard point given as pg of deoxyribonucleoside kinase. Each standard point carries the pg(X);Ct(y) value, FIG. 4.

Example 3 hrTK1 Standard Curve According to Detection System 2

A standard curve was constructed representing catalytic activity values from, 200 pg, 20 pg and 2 pg of hrTK1. A 0 pg standard point was included as a negative control. Briefly, enzyme mixes were prepared to contain the hrTK1 standard point; NdPK and TMPK as for Example 1. MMX's were prepared as for Example 1 except that 0.4 U of Taq DNA polymerase replaces the Klenow DNA polymerase and that oligonucleotides were according to Table 5. Finally, respective standard point enzyme mix was added to the each dedicated MMX. The 200 pg enzyme mix of was included in the NTC. From each standard point mix 25 µl was dispensed into three PCR tubes. Tubes were capped and placed into the PCR instrument. Cycling profile was: (1) Hold at 42° C. for 1 min, (2) Hold at 35° C. for 1 min, (3) Cycling: 37° C. for 30 s→37° C. 30 s with signal acquisition to the SYBR GreenI®/FAM channel (excitation at 470 nm detection at 510 nm). Each 1 min cycle was repeated 60 times. Total assay time 65 minutes.

TABLE 5

Oligonucleotides and DNA polymerase for hrTK1 determination according to detection system 2 different from Example1.

| Reagent | Assay concentration | mix | Comments |
| --- | --- | --- | --- |
| SEQ ID: 2 Primer O25XTTM | 400 nM | Oligo-nucleotide mix | Delivered by Cybergene AB, Sweden. |
| SEQ ID: 1 Template O24TTTM | 500 nM | Oligo-nucleotide mix | Delivered by Cybergene AB, Sweden. |
| SEQ ID: 3 Probe O26PTTM | 300 nM | Oligo-nucleotide mix | 5'-nucleotide labelled with 6-FAM. 3'-nucleotide labelled with -BHQ1. Delivered by Cybergene AB, Sweden. |
| Taq DNA polymerase | 0.4 U per reaction | | From Fermentas UAB. Dreamtaq ® EP0701. |

Results

Figure 12:
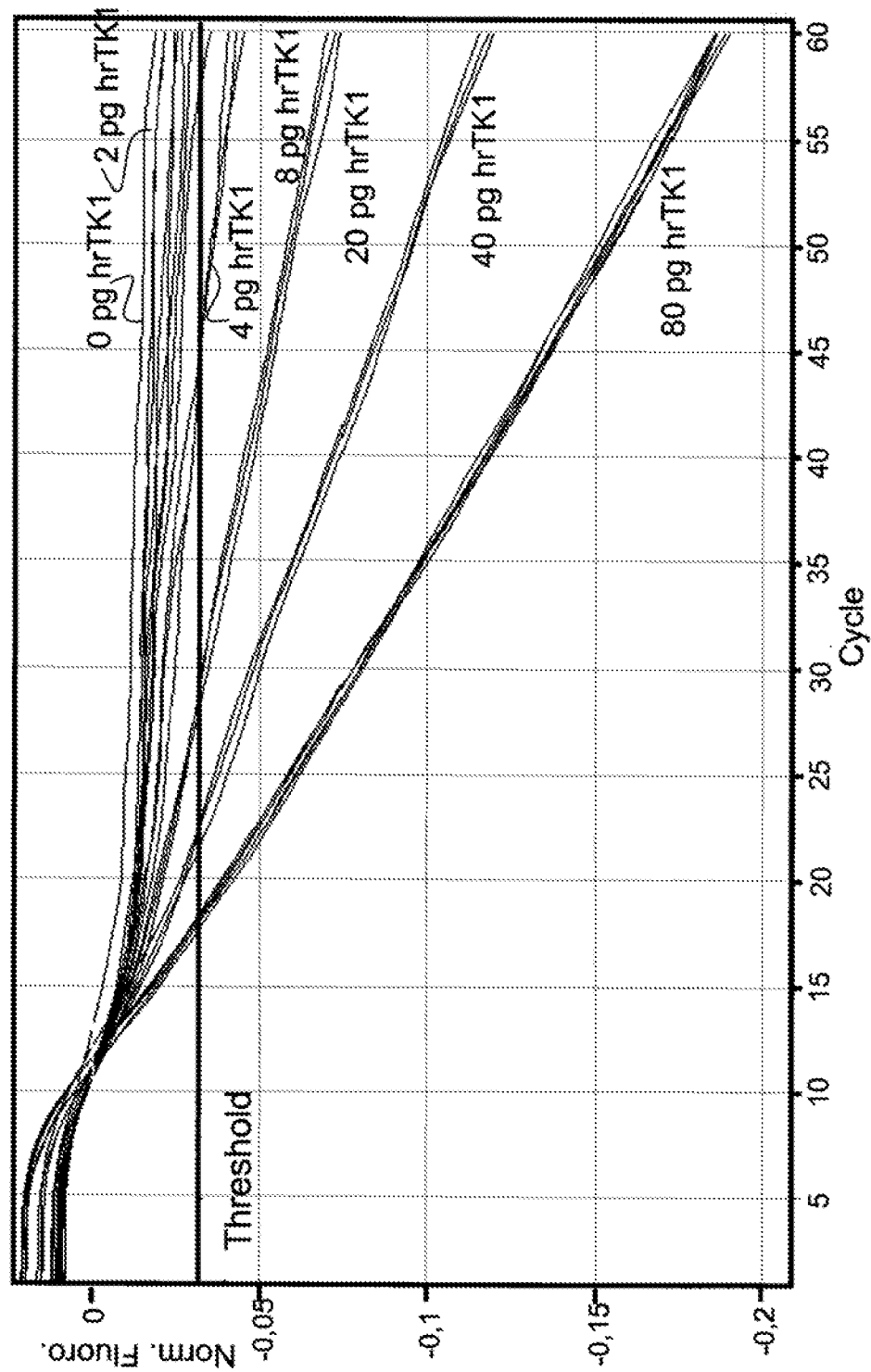
FIG. 12 Linearly and dynamic tube normalised fluorescence obtained by real-time fluorescence capture reaching threshold level Ct from Example 10.

FIG. 12 depicts the raw fluorescence obtained from this experiment. The raw fluorescence was standard normalised i.e. only calculated over the first five cycles and linearized, starting from cycle 1, FIG. 5. In order to determine the number of Ct's for respective standard point, (on the X-axis), a threshold level was selected for 2 pg after approx. 60 minutes. The threshold was found to be 0.12 of normative fluorescence units (Y-axis). Ct values was determined using the built in software Rotor-gene v. 6.01 for the chosen threshold. A logarithmic regression plot of the mean of each standard point Ct (Y-axis) and pg hrTK1 value (X-axis), gave an $R^2$ value of 0.98 indicating the validity of using the obtained standard curve to determine real sample Unit activity values. The assay precision performance (CV %) results are summarised below, Table 6. Note that Ct values correspond to the activity from picograms of hrTK in the reaction. Knowing that the specific activity of this specific construct is 2.1 µmol/min/mg of enzyme it is possible to deduce the actual catalytic concentration. However since there is yet no standardization for TK activity to follow the International Unit definition i.e. 1 U=1 µmol/min/l, for simplistic reasons only corresponding "picogram" activity is given in this example.

TABLE 6 hrTK1 standardpoints - performance characteristicsExample 4 dCK standard curve from HrdCK according to detection system 2.

| Amount of TK activity given in equivalent picograms | Ct | X | s | CV % |
| --- | --- | --- | --- | --- |
| 200 | 20.65 | 20.22 | 0.38 | 1.88% |
| 200 | 19.93 | | | |
| 200 | 20.08 | | | |

TABLE 6-continued hrTK1 standardpoints - performance characteristicsExample 4 dCK standard curve from HrdCK according to detection system 2.

| Amount of TK activity given in equivalent picograms | Ct | X | s | CV % |
|---|---|---|---|---|
| 20 | 34.65 | 34.76 | 0.22 | 0.63% |
| 20 | 35.01 | | | |
| 20 | 34.61 | | | |
| 2 | 59.66 | 58.05 | 1.44 | 2.48% |
| 2 | 56.89 | | | |
| 2 | 57.61 | | | |

A standard curve was constructed representing HrdCK catalytic activity values from 20000 pg; 2000 pg; 200 pg, 20 pg and 2 pg of enzyme. A 0 pg standard point was included as a negative control. Briefly, enzyme mixes were prepared to contain the standard point; NdPK and dCMPK as given in Example's 1 and 2. 3.2*25 µl MMX's were prepared at room temperature in a 1.5 ml polypropylene micro centrifuge tube for each standard point (including the 0 pg dCK negative control) by mixing buffer-, substrate-, oligonucleotide mix (Table 7), together with 0.4 U of Taq DNA polymerase. Note that oligonucleotides were replaced with those given in Table 7 below. Finally, the enzyme mix from respective standard point was added to the MMX. The 20000 pg enzyme mix of was included in the NTC MMX. 25 µl of MMX and standard point mix was dispensed into three PCR tubes. Tubes were capped and placed into the real-time PCR instrument. Cycling profile was: (1) Hold at 42° C. for 1 min, (2) Hold at 35° C. for 1 min, (3) Cycling: 37° C. for 30 s→37° C. 30 s with signal acquisition to the JOE channel (excitation at 530 nm detection at 555 nm). Each cycle was repeated 60 times. Total assay time 65 minutes.

TABLE 7

MMX for determination of dCK catalytic concentration according to detection system2.

| Reagent | Assay concentration | mix | Comments |
|---|---|---|---|
| SEQ ID: 5 Primer O28XCTM | 400 nM | Oligo-nucleotide mix | Delivered by Cybergene AB, Sweden. |
| SEQ ID: 4 Template O27TCTM | 500 nM | Oligo-nucleotide mix | Delivered by Cybergene AB, Sweden. |
| SEQ ID: 6 Probe O29PCTM | 400 nM | Oligo-nucleotide mix | 5'-nucleotide labelled with TET. The 3'-nucleotide labelled with -BHQ1. Delivered by Cybergene AB, Sweden. |

Results.

Figure 7:
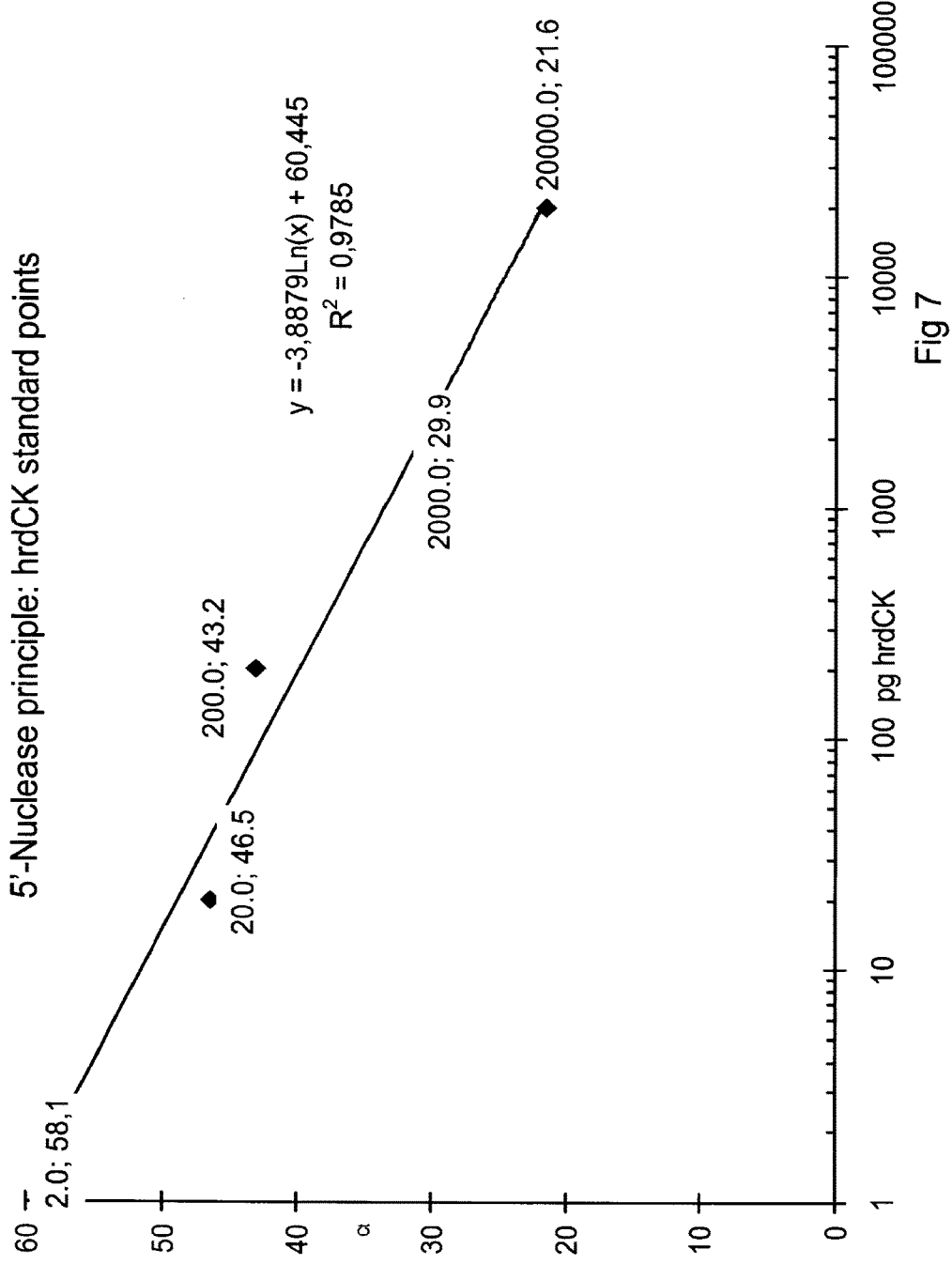
FIG. 7 Linear regression on a logarithmic scale on mean Ct values from Example 4 for hrdCK standard points.

Ct values for each standard point of pg dCK value were obtained as described in Example 3. The logarithmic regression of the linear fluorescence gives an $R^2$ value of 0.98 indicating the validity of using this standard curve to determine dCK activity values from real clinical samples. Precision performance results are summarised in Table 8. Linear regression on a logarithmic scale is depicted in FIG. 7.

TABLE 8 hrdCK standardpoints - Precision performance

| Activity from: -- of hrdCK | Ct | X | s | CV % |
|---|---|---|---|---|
| 20000 pg | 21.76 | 21.61 | 0.17 | 0.80% |
| 20000 pg | 21.65 | | | |
| 20000 pg | 21.42 | | | |
| 2000 pg | 29.30 | 29.91 | 0.81 | 2.69% |
| 2000 pg | 30.82 | | | |
| 2000 pg | 29.60 | | | |
| 200 pg | 43.13 | 43.15 | 0.87 | 2.01% |
| 200 pg | 42.30 | | | |
| 200 pg | 44.03 | | | |
| 20 pg | 46.99 | 46.46 | 0.47 | 1.02% |
| 20 pg | 46.33 | | | |
| 20 pg | 46.07 | | | |
| 2 pg | 58.10 | 58.09 | 1.24 | 2.13% |
| 2 pg | 56.85 | | | |
| 2 pg | 59.33 | | | |

Example 5 hrTK1 Standard Curve According to Detection System 3

Standard curve were constructed representing hrTK1 catalytic activity values from, 200 pg, 20 pg and 2 pg of enzyme. Briefly, enzyme mixes for respective nucleoside kinase were prepared to contain the nucleoside standard point together with NdPK and TMPK as described in Example 3. A 3.2*25 µl MMX's were prepared according to Example 3 with the following exceptions: DNA-dependant DNA polymerase and oligonucleotides were replaced by those given in Table 9 below.

TABLE 9

MMX for determination of hrTK1 according to detection system 3 and different from Example 3.

| Reagent | Assay concentration | Comments |
|---|---|---|
| SEQ ID: 9 Primer O33XTMB | 300 nM | |
| SEQ ID: 8 Template O32TTMB | 400 nM | |
| SEQ ID: 10 Molecular beacon O35PTMB | 600 nM | 5'-nucleotide labelled with FAM. 3'-nucleotide labelled with -Dabcyl. Delivered by Cybergene AB, Sweden. |
| Bsm DNA Polymerase | 1 U per reaction | From FERMENTAS AB |

Finally, the enzyme mix from respective standard point was added to respective MMX. The 200 pg enzyme mix of was included in the NTC. Tubes were closed and placed into the real-time PCR instrument. Cycling profile was: (1) Hold at 42° C. for 1 min, (2) Hold at 35° C. for 1 min, (3) Hold at 37° C. for 15 min, (4) Cycling: 37° C. for 30 s→37° C. 30 s with signal acquisition to the FAM channel repeated 90 times. Total assay time 108 minutes. Threshold selected for 0 pg at 90 minutes.

Results

Figure x depicts the decrease in raw fluorescence from displaced FAM/Dabcyl molecular beacon probes in real-time. Threshold is set at 0.012 normative fluorescence units. FIG. 14 shows the logarithmic regression of mean of obtained $C_t$ values from the three standard points.

$R^2$ value is 0.96. The logarithmic regression of the linear fluorescence gives an $R^2$ value of 0.98 indicating the validity of using this standard curve to determine dCK activity values from real clinical samples.

Example 6

HrdCK Standard Curve According to Detection System 3

Standard curve were constructed representing hrdCK catalytic activity values from 2000 pg, 200 pg; and 20 pg and 2 pg of enzyme. A 0 pg standard point was included as a negative control and for setting of the threshold normalised fluorescence value. Briefly, enzyme mixes for respective nucleoside kinase were prepared to contain the nucleoside standard point; NdPK and dCMPK according to Examples 2 and 4. A 3.2*25 μl MMX's were prepared according to Example 5 with the exception of the oligonucleotides which were according to Table 10 below.

TABLE 10

MMX for determination of hrdCK catalytic concentration according to detection system 3 and different from Example 2 and 4.

| Reagent | Assay concentration | Comments |
| --- | --- | --- |
| SEQ ID: 9 Primer O33XTMB | 400 nM | |
| SEQ ID: 11 Template O42TCMB | 300 nM | |
| SEQ ID: 10 Molecular beacon O35PTMB | 600 nM | 5'-nucleotide labelled with FAM. 3'-nucleotide labelled with -Dabcyl. Delivered by Cybergene AB, Sweden. |

Finally, the enzyme mix from respective nucleoside and respective standard point were added to respective MMX. The 200 pg enzyme mix of was included in the NTC MMX. 25 μl was dispensed into three 100 μl PCR tubes from each standard point, capped and placed into the real-time PCR instrument. Cycling profile was: (1) Hold at 42° C. for 1 min, (2) Hold at 35° C. for 1 min, (3) Cycling: 37° C. for 30 s→37° C. 30 s with signal acquisition to the JOE channel. Each cycle was repeated 90 times. Total assay time 108 minutes.

Results.

Normalisation of fluorescent signal is from cycle 1. Threshold was selected for 0 pg after 90 minutes. The logarithmic regression of mean $C_t$ values from the four standard points. $R^2$ value is 0.96.

Example 7

Multiplex Determination of hrTK1 and hrdCK According to Detection System 2 Using Mixes with Different Amounts of Respective Deoxyribonucleoside Kinase Standard curves were constructed from a mix with different hrTK1 and hrdCK catalytic activity values given in Table 11 below. Briefly, enzyme mixes were prepared to comprise each standard point hrTK1/hrdCK point together with NdPK, TMPK and dCMPK according to Examples 1 and 2. MMX was prepared according to Examples 3 with the following exceptions: oligonuclotides from Example 4 was included and NdPK was 0.02 U/reaction.

TABLE 11

Multiplex mixes of TK and dCK

| Mix # | Amount of TK in pg per reaction FAM signal (at 510 nm) | Amount of dCK in pg per reaction TET signal (at 534 nm) |
| --- | --- | --- |
| 1 | 200 | 20 |
| 2 | 20 | 200 |
| 3 | 2 | 0 |
| 4 | 200 | 2000 |
| 5 | 2 | 20 |
| 6 | 200 | 200 |
| 7 | 20 | 2000 |
| 8 | 0 | 2000 |
| 9 | 200 | 0 |
| NTC mix | 200 | 200 |

Finally, respective enzyme mix was added to each MMX. Tubes capped and placed into the real-time PCR instrument. Cycling profile was: (1) Hold at 42° C. for 2 min, (2) Hold at 35° C. for 1 min, (3) Hold at 37° C. for 15 min (4) Cycling: 37° C. for 30 s→37° C. 30 s with signal acquisition to the FAM/SYBR channel and from the JOE channel respectively. Each cycle was repeated 90 times. Total assay time 108 minutes. Start normalisation from cycle 1. Threshold selected for 0 pg TK after 90 minutes.

Results

Figure 8:
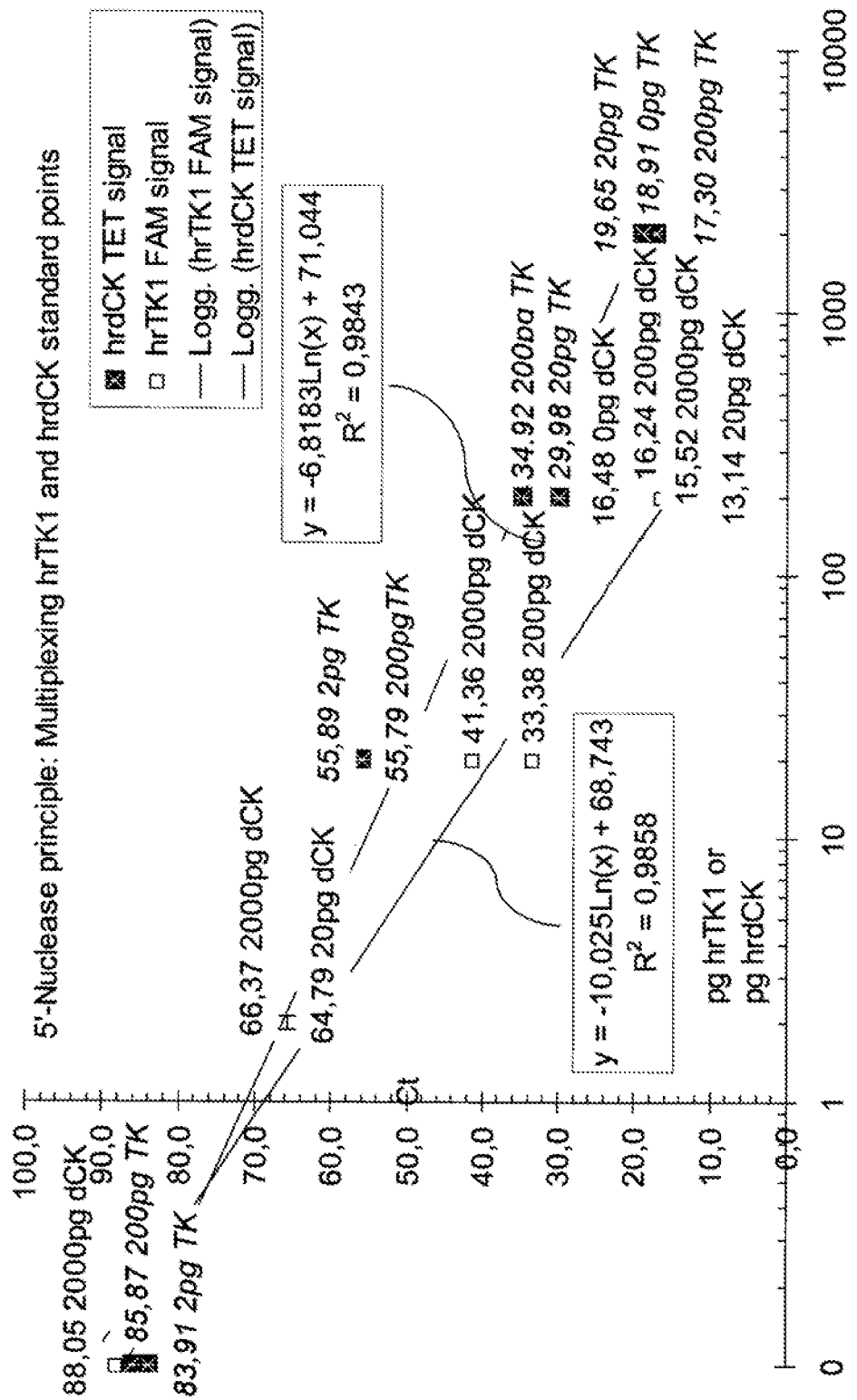
FIG. 8 Linear regressions on a logarithmic scale from Example 7, multiplexing hrTK1 together with hrdCK.

FIG. 8 shows the linear regression on a logarithmic scale results from the multiplexing experiment. On the Y-axis is number of Ct's needed for detection. X-axis is the arbitrary "pg" activity from respective deoxyribonucleoside kinase.

The results clearly indicate that the amount of either deoxyribonucleoside kinase has no affect on the primer extension efficiency of the other. The different slopes of the two deoxyribonucleoside kinase involved are probably due to the different specific activities that these enzymes may exhibit.

Example 8

Determination of Wildtype TK Catalytic
Concentrations in Canine Serum Samples
According to Detection System 2 and Correlation
to TK-REA Method Canine serum samples with a previous diagnosed malignant disease were tested for hrTK1 catalytic concentrations according to detection system 2. Each serum has previously been measured by the TK-REA method. A standard curve was included with catalytic activities from 200 pg, 20 pg and 2 pg of hrTK1. The experiment was carried out according to Example 2 with the following exceptions: 1) Serum samples TK dilution buffer replaced hrTK1 and serum was added to a final concentration of 5% i.e. 1.25 µl of serum was included in each reaction (4 µl of serum per MMX/enzyme mix); 2) Cycling profile was according to Example 1. Normalisation was from cycle 1. Threshold selected for 0 pg TK after 90 minutes.

Results

Figure 9:
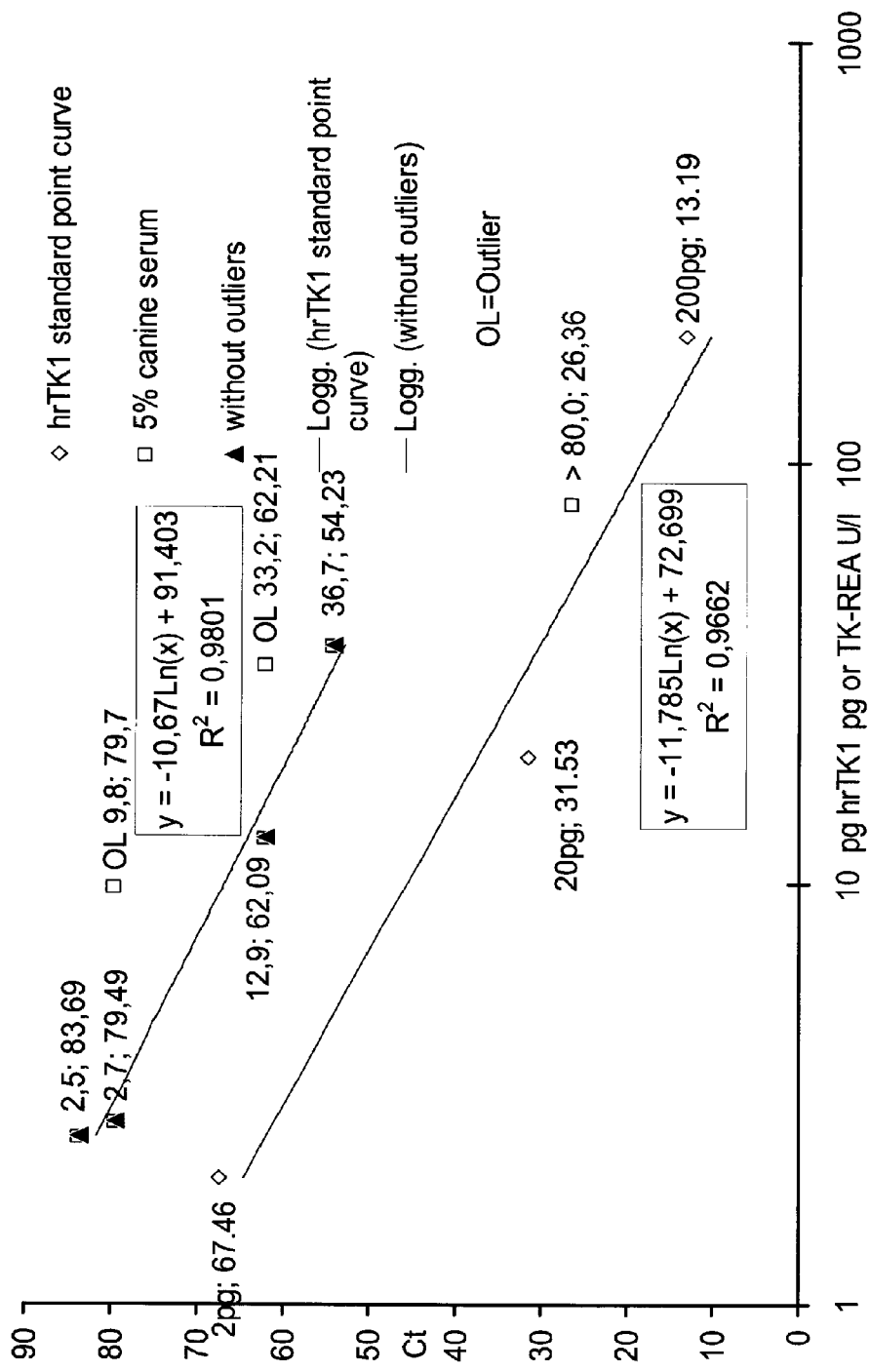
FIG. 9 Linear regressions on a logarithmic scale from measuring TK1 in canine serum samples and hrTK1 standard points used in Example 8.

Ct's for each standard point and serum sample was obtained using the Rotor-Gene v.6.1 software (Qiagen GmbH. Linear regression on a logarithmic scale was executed on the samples and on the standard curve, FIG. 9. It could immediately be seen that 2 serums could not fit the TK-REA U/l value that was originally obtained. A third serum having a value of ">80" could neither be fitted in since there was no way this could fit into the line. These three serums therefore were deemed "outliers" and a regression line excluding these three serum was constructed. The equation for the standard points and for the serum samples, excluding three outliers (">80", 33.2 and 9.8 TK-REA U/l), differs only by 2.4 Ct's with respect to the slope of the curve. It is evident that the two curves share the same slope. In estimating the U/l resulting from serum in this Example, using the method according to the invention, this is done solely using the regression line equation for the serum points i.e. equation $y=-10.79\ \text{Ln}(x)+93.784$. Correlating pg hrTK1 to the serum sample regression line is solved by using the equation $U/l=e^{((11.79\ \ln(pg(x))+21.085)/10.67)}$ with respect to the "pg" activity amount of TK given for the standard point regression curve. In FIG. 9 each standard point is represented with ["pg" TK(X); Ct (Y)] and each serum is represented with ["TK-REA U/l"TK(X); Ct (Y)] The $R^2$ value is given for each curve. "OL" in FIG. 9 denotes Outlier serum. Results from FIG. 9 together with precision data are tabulated in Tables 12 and 13. Interestingly the ">80 U/l" sample could be estimated using the method according the invention to carry 450 U/l TK-REA corresponding units without any need for dilution by extrapolation to the prolonged serum regression line.

TABLE 12

Estimated TK-REA U/l value for the pg amount
of hrTK1 and standard point precision data

| hrTK1 Stdpoint | Estimated TK-REA U/l | X Ct | CV % |
|---|---|---|---|
| 200 pg | 2013 | 13.19 | 1.23% |
| 20 pg | 158 | 31.53 | 4.49% |
| 2 pg | 12.4 | 67.46 | 9.28% |

TABLE 13

Correlation of canine serum TK-REA U/l values to values obtained
using the method according to detection system 2 standard
curve with test precision data (intra assay CV %).

| | Given | | | Estimated U/l Given | Corrected | Serum used |
|---|---|---|---|---|---|---|
| Serum # | TK-REA U/l | X Ct | CV % | U/(1.25 µl) | U/l | Inrgression |
| 5928372 | 33.2 | 62.21 | 5.62% | 4.15E−5 | 15.4 | No |
| 5927710 | 9.8 | 79.70 | 5.06% | 1.23E−5 | 3.0 | No |
| 8092194 | >80 | 26.36 | 3.37% | >1.0E−4 | 444 | No (see note) |
| 5924810 | 12.9 | 62.09 | 5.32% | 1.61E−5 | 15.6 | Yes |
| 8092350 | 2.5 | 83.69 | 5.39% | 3.13E−6 | 2.1 | Yes |
| 8093159 | 36.7 | 54.23 | 2.68% | 4.59E−5 | 32.6 | Yes |
| 5926861 | 2.7 | 79.49 | 5.99% | 3.28E−6 | 3.1 | Yes |

Example 9

Determination of Serum Spiked hrTK1 Samples Using the SYBR Green I Technical Principle, i.e. Detection System 1

Serum from canines, for which TK1 activity previously had been measured using the TK-REA product from Diasorin s.r.I., (Saluggia Italy), was tested using the SYBR Green technical principle. Standard curve samples, representing catalytic activity from 40 pg, 20 pg, 4 pg, 2 pg and 0 pg of hrTK1, spiked with 10% human normal serum from a blood donor, were measured alongside the serum samples (final 10%). The 0 pg spiked standard point sample was included as a negative control and threshold determinant of normalised fluorescence. Briefly, enzyme mixes were prepared to contain 0.002 U NdPK, and 18 ng per reaction of dTMP kinase, each hrTK1 standard point sample or each serum sample. Buffer-, substrate- and oligonucleotide mixes were prepared according to Table 3. A MMX for each sample was prepared at room temperature in a 1.5 ml polypropylene microcentrifuge tube by mixing water, mixe's and 0.5 U of Klenow exo⁻ DNA polymerase (Fermentas AG). A MMX 200 pg hrTK1 the enzyme mix standard point sample was used as No-Template-Control (NTC).

TABLE 14

MMX for determination serum spiked hrTK1 using the SYBER GreenI technical principle, i.e. according to detection system 1.

| Reagent | Assay concentration | mix | Comments |
|---|---|---|---|
| deionised water | — | — | |
| Buffer: Tris-HCl pH 8.0 (25° C.) | 50 mM | Buffer mix | Ambion 1M stock, AM9855G |
| MgCl$_2$ | 5.0 mM | Buffer mix | Ambion 1M stock, AM9530G |
| BSA | 0.5% | Buffer mix | Sigma-Aldrich AG, A-6003. 10% stock solution. Heat inactivated @ 56° C. 20'. |
| DTT | 8.0 mM | Buffer mix | Pharamcia Biotech 17-131024 |
| Thymidine (T) | 100 µM | Substrate mix | Sigma-Aldrich AG, 89270 |
| deoxyCytidine (dC) | 100 µM | Substrate mix | Sigma-Aldrich AG, D3897 |
| SYBR GreenI | 1X | Substrate mix | InVitrogen Inc. S32717 Stock is 10000 according to manufacturers Certificate of Analysis |
| dATP | 100 µM | Substrate mix | Fermentas UAB. Stock 0.1M R0141 |
| dGTP | 100 µM | Substrate mix | Fermentas UAB. Stock 0.1M R0161 |
| dCTP | 100 µM | Substrate mix | Fermentas UAB. Stock 0.1M R0151 |
| ATP | 4.0 mM | Substrate mix | Supplied by Uppsala University Dept. of Medical Sciences |
| SEQ ID: 7 Template O31TTSG | 300 nM | Oligonucleotide mix | Cybergene AB, Sweden. |
| SEQ ID: 9 Primer O33XTMB | 600 nM | Oligonucleotide mix | Cybergene AB, Sweden. |
| dTMP Kinase | 18 ng per reaction | Enzyme mix | Recombinant bacterial. Original cDNA cloned into pET14b. Protein expressed and purified from *E. coli* host BL21-(DE3) pLys. |
| NdPK | 0.002 U per reaction | Enzyme mix | Sigma-Aldrich AG N0379, purified from bakers yeast. |
| hrTK1 | 2 pg; 4 pg; 20 pg; 40 pg | Enzyme mix | Met-106. Original human cDNA cloned into pPET14b to yield pETKW3. Protein expressed and purified from *E. coli* host BL21-(DE3) pLys. |
| Klenow exo⁻ fragment | 0.5 U per reaction | | Fermentas AG, EP0422 |

Samples were dispensed; tubes were closed and placed into the real-time PCR instrument. Run profile was: (1) Hold at 40° C. for 1 min, (2) Hold at 30° C. for 1 min, (3) Hold at 35° C. for 10 min (4) Cycling: 35° C. for 30 s→37° C. 30 s with signal acquisition to the SYBR GreenI® channel (excitation at 470 nm detection at 510 nm). Each cycle was repeated 60 times.

Results.

Figure 10:
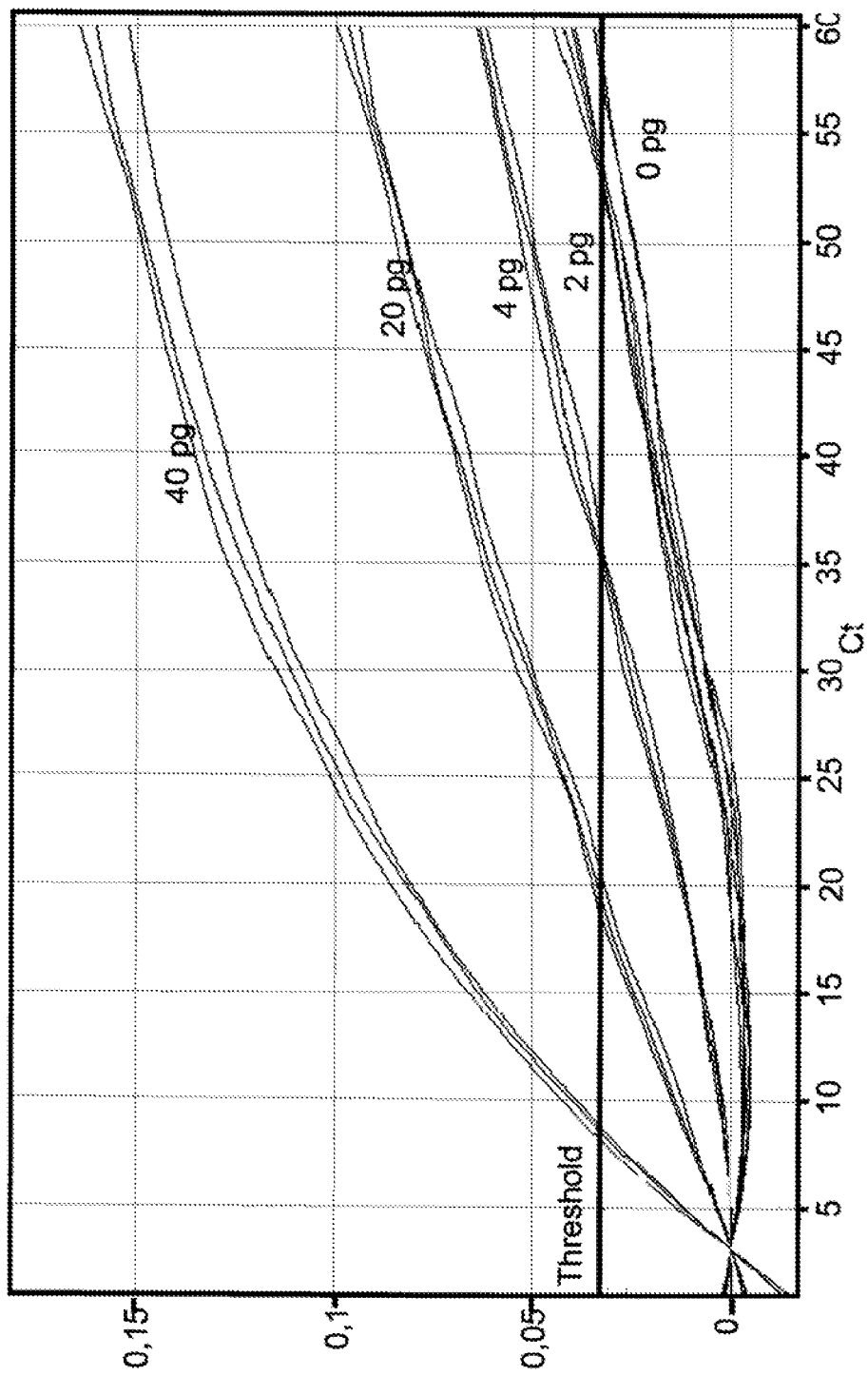
FIG. 10 Linearly normalised fluorescence curves obtained by real-time fluorescence capture reaching threshold level Ct from Example 9.
Figure 11:
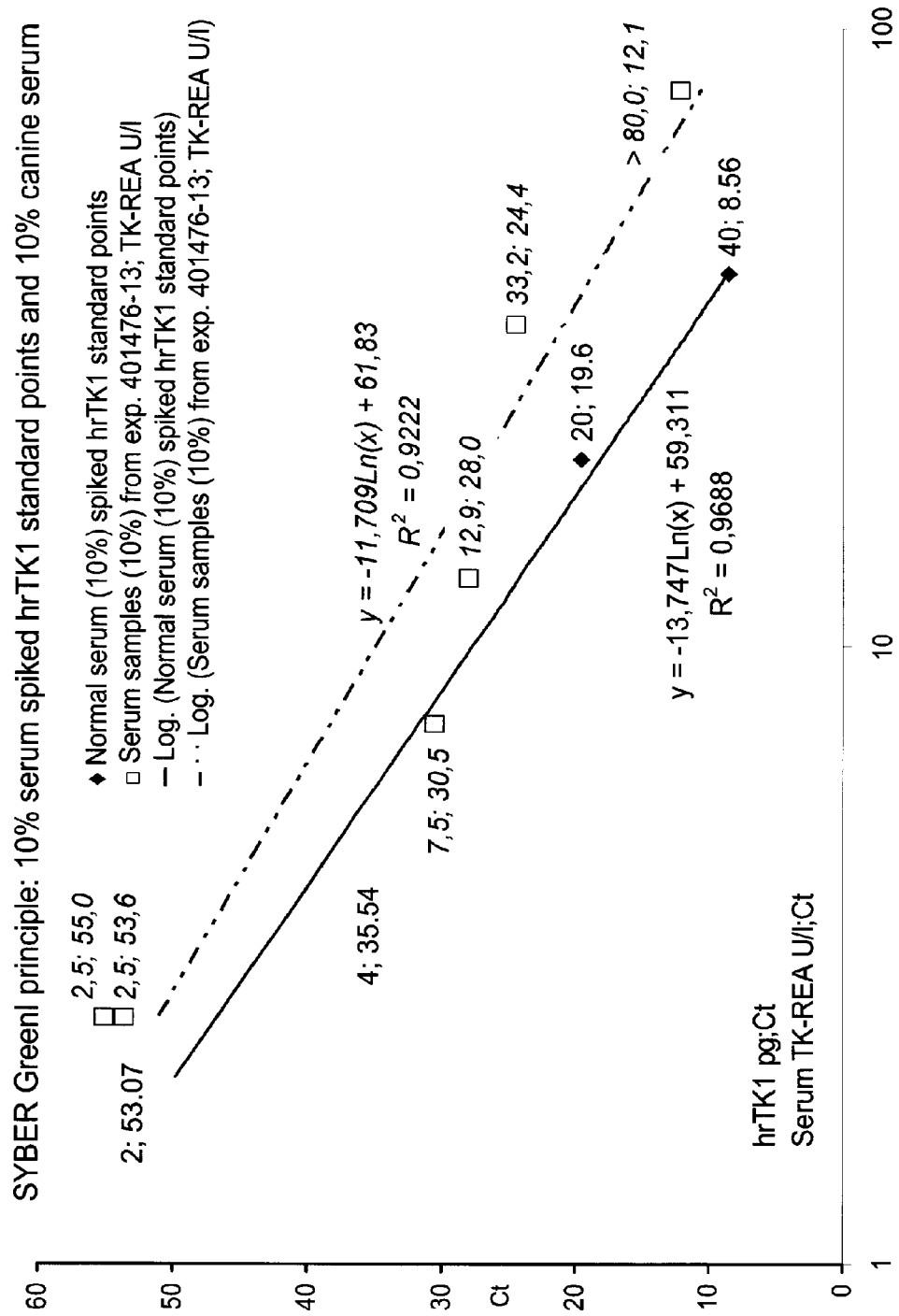
FIG. 11 Linear regressions on a logarithmic scale on mean Ct values from Example 9 from pathogenic canine serum and hrTK1 standard points.

Normalisation of fluorescence was acquired and made linear from cycle 1 using standard normalisation, FIG. 10, (i.e. mean fluorescence from the first five cycles were used to determine the background fluorescence which is deduced from the fluorescence obtained from the subsequent cycles according to the software provider). NTC threshold (cut-off) is 4% of the sample with the highest increase in fluorescence. Ct values were determined using the built in software Rotor-gene v. 6.01 (Corbett Research, Australia) for the chosen threshold. Threshold was selected for 0 pg of hrTK1 crossing after approximately 56 cycles (Ct's). In this example a threshold at 0.03295 normative fluorescence units was obtained. FIG. 11 depicts linear regression on a logarithmic scale of Ct values obtained. On the X-axis are given the activity from respective sample, either as pg of hrTK1 or as TK-REA U/l. Each sample point carries the pg/TK-REA U/l(X);Ct(y) value. An linear regression and $R^2$ score of 0.9688 was obtained for the serum spiked hrTK1 standard point samples indicating that the correlation is good enough for determining the amount of TK U/l in a sample. A Students t-test was applied to the two separate regression curves in order to further determine the relationship between the slopes. Due to the small data-set the t-test was calculated manually. The test was performed with equal variance but with unequal sample size. A score of 0.07 on the data set indicated that there is a high probability that the slopes may be considered as being equal.

Example 10 hrTK1 Standard Curve Obtained Using the Strand Displacement Technical Principle, i.e. According to Detection System 3

A standard curve was constructed representing catalytic activity values from, 80 pg, 40 pg, 20 pg, 8 pg, 4 pg, 2 pg and 0 pg of hrTK1. Briefly, MMX's were prepared for each standard point as described in example 2 and Table 7.

TABLE 15

MMX for determination of hrTK1 according to the displacement principle

| Reagent | Assay concentration | mix | Comments |
| --- | --- | --- | --- |
| deionised water | — | — | |
| Tris-HCl pH 8.0 (25° C.) | 50 mM | Buffer mix | Ambion 1M stock, AM9855G |
| MgCl2 | 7.0 mM | Buffer mix | Ambion 1M stock, AM9530G |
| KCL | 10 mM | Buffer mix | Ambion 2M stock, AM9640G |
| BSA | 0.5% | Buffer mix | Sigma-Aldrich AG, A-6003. 10% stock solution. Heat inactivated @ 56° C. 30'. |
| DTT | 8.0 mM | Buffer mix | Pharamcia Biotech 17-131024 |
| Thymidine (T) | 100 µM | Substrate mix | Sigma-Aldrich AG, 89270 |
| deoxyCytidine (dC) | 100 µM | Substrate mix | Sigma-Aldrich AG, D3897 |
| dATP | 100 µM | Substrate mix | Fermentas AG. Stock 0.1M R0141 |
| dCTP | 100 µM | Substrate mix | Fermentas AG. Stock 0.1M R0151 |
| dGTP | 100 µM | Substrate mix | Fermentas AG. Stock 0.1M R0161 |
| ATP | 4.0 mM | Substrate mix | Supplied by Uppsala University Dept. of Medical Sciences |
| dTMP Kinase | 18 ng per reaction | Enzyme mix | Recombinant bacterial. Original cDNA cloned into pET14b. Protein expressed and purified from *E. coli* host BL21-(DE3) pLys. |
| NdPK | 0.002 U per reaction | Enzyme mix | From Sigma Aldrich AG N0379 purified from bakers yeast. |
| hrdTK1 | 2 pg; 4 pg; 8 pg 20 pg; 40 pg, 80 pg | Enzyme mix | Met-106 variant. Original human cDNA cloned into pPET14b vector to yield pETKW3. Protein expressed and purified from *E. coli* host BL21-(DE3) pLys. |
| SEQ ID: 9 Primer O33XTMB | 400 nM | Oligonucleotide mix | Delivered by Cybergene AB, Sweden |
| SEQ ID: 8 Template O32TTMB | 300 nM | Oligonucleotide mix | Delivered by Cybergene AB, Sweden |
| SEQ ID: 10 Molecular beacon O35PTMB | 600 nM | Oligonucleotide mix | 5'-nucleotide labelled with FAM. 3'-nucleotide labelled with - BHQ1. Delivered by Cybergene AB, Sweden |

TABLE 15-continued

MMX for determination of hrTK1 according to the displacement principle

| Reagent | Assay concentration mix | Comments |
|---|---|---|
| Bsm DNA polymerase | 1 U per reaction | From Fermentas AG |

The 80 pg hrTK1 containing enzyme mix of was included in the NTC. MMX's were dispensed, tubes were closed and placed into the real-time PCR instrument. Cycling profile was: (1) Hold at 42° C. for 1 min, (2) Hold at 35° C. for 1 min, (3) Hold at 37° C. for 15 min, (4) Cycling: 37° C. for 30 s→37° C. 30 s with signal acquisition to the FAM channel repeated 90 times. Total assay time 108 minutes. Threshold selected for 0 pg at 90 minutes.

Results

Figure 13:
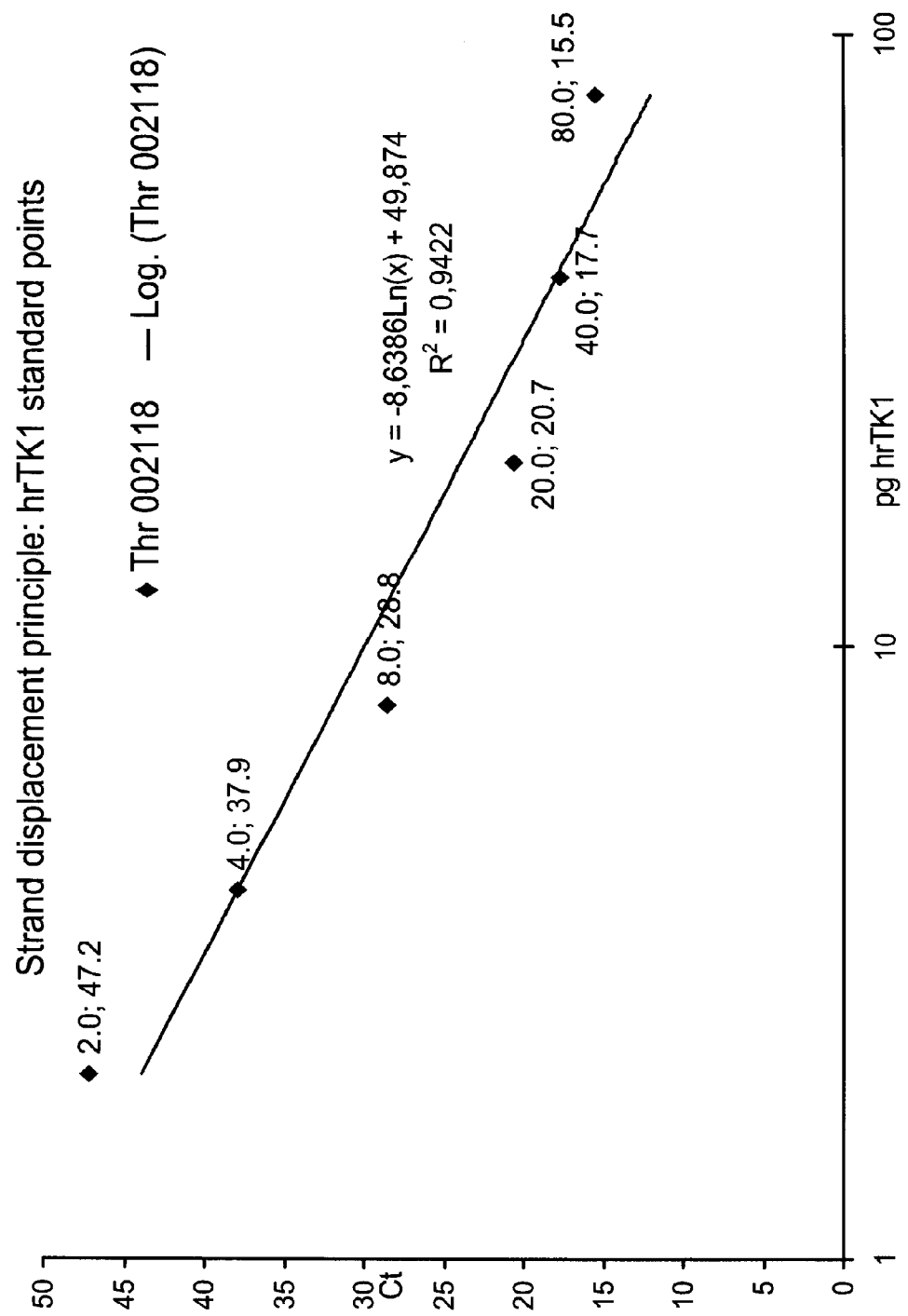
FIG. 13 Linear regression on a logarithmic scale on mean Ct values from Example 10 for hrTK1 standard points.

FIG. 12 depicts the decrease from normalised fluorescence from displaced FAM molecular beacon hairpin probes in real-time. The normalisation method used was Dynamic tube normalisation according to the software providers instruction (Corbett-Research) Threshold is set at—(minus) 0.02118 normative fluorescence units. FIG. 13 shows the linear regression on a logarithmic scale of the mean $C_t$ values obtained from the six standard points. $R^2$ value is 0.9422 indicating that the standard curve may be applied for determination of TK activities in clinical samples from serum or plasma.

REFERENCES

Eriksson S, Munch-Petersen B, Johansson K, Eklund H. Structure and function of cellular deoxyribonucleoside kinases. Cell Mol Life Sci. 2002 59(8):1327-46.

Topolcan O and Holubec L. Jr. The role of thymidine kinase in cancer diseases. Expert. Opin. Med. Diagn. 2008 2(2): 129-141

Patents: US2008/0248472, EP1385005, WO2009/063254

The invention claimed is:

1. A kit comprising: (i) a DNA dependent DNA polymerase, (ii) at least one natural deoxynucleoside, and (iii) a detection system comprising a DNA template molecule, a DNA primer molecule, and a fluorescent moiety capable of being displaced from, or bound to, dsDNA synthesized by said DNA dependent DNA polymerase.

2. A kit according to claim 1, further comprising at least one phosphotransferase.

3. A kit according to claim 1, further comprising at least one modified deoxynucleoside.

4. A kit according to claim 1, further comprising at least one modified deoxynucleoside chosen from deoxythymidine and/or deoxycytidine.

5. A kit according to claim 1, wherein the fluorescent moiety is coupled to a single stranded DNA probe.

6. A kit according to claim 1, wherein the fluorescent moiety and a quenching moiety are coupled to a single stranded DNA probe.

7. A kit according to claim 1, wherein the fluorescent moiety is a double stranded DNA surface binding or intercalating molecule.

8. A kit according to claim 1, wherein the fluorescent moiety bound to the single stranded DNA probe is quenched when said probe is in its intact form.

9. A kit according to claim 1, wherein the DNA dependent DNA polymerase has 5' to 3' exonuclease activity.

10. A kit according to claim 1, wherein the fluorescent moiety bound to the single stranded DNA probe attains maximum fluorescence when in its intact form and hybridized to its target template.

11. A kit according to claim 1, wherein the DNA dependent DNA polymerase is a displacing active polymerase.

* * * * *

SEQUENCE LISTING

```
<160> NUMBER OF SEQ ID NOS: 21

<210> SEQ ID NO 1
<211> LENGTH: 36
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(36)
<223> OTHER INFORMATION: Template O24TTTM

<400> SEQUENCE: 1
tactaagcac tgtctttctc taagatcacc gtcctg                36

<210> SEQ ID NO 2
<211> LENGTH: 10
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(10)
<223> OTHER INFORMATION: Primer O25XTTM

<400> SEQUENCE: 2
acggtgatct                10

<210> SEQ ID NO 3
<211> LENGTH: 13
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(13)
<223> OTHER INFORMATION: Probe O26PTTM

<400> SEQUENCE: 3
```
aagacagtgc tta                                                          13

<210> SEQ ID NO 4
<211> LENGTH: 35
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(35)
<223> OTHER INFORMATION: Template O27TCTM

<400> SEQUENCE: 4
ttcaaccaca ctttctctga cgtctatcag cctgt                                  35

<210> SEQ ID NO 5
<211> LENGTH: 11
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(11)
<223> OTHER INFORMATION: Primer O28XCTM

<400> SEQUENCE: 5
ctgatagacg t                                                            11

<210> SEQ ID NO 6
<211> LENGTH: 12
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(12)
<223> OTHER INFORMATION: Probe O29PCTM

<400> SEQUENCE: 6
aagtgtggtt ga                                                           12

<210> SEQ ID NO 7
<211> LENGTH: 80
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(80)
<223> OTHER INFORMATION: Template O31TTSG

<400> SEQUENCE: 7
tgtggtcgtt gcgtttgctg cctttgcttt ctgctgcttt tgctctcctt tgtctgcgtc       60
ccttttgtta agctcatgag                                                   80

<210> SEQ ID NO 8
<211> LENGTH: 40
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(40)

<223> OTHER INFORMATION: Template O32TTMB

<400> SEQUENCE: 8
tgctgttctg tgttgtcgtt ttttttaag ctcatgaggt           40

<210> SEQ ID NO 9
<211> LENGTH: 10
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(10)
<223> OTHER INFORMATION: Primer O33XTMB

<400> SEQUENCE: 9
ctcatgagct           10

<210> SEQ ID NO 10
<211> LENGTH: 21
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(21)
<223> OTHER INFORMATION: Molecular beacon O35PTMB

<400> SEQUENCE: 10
tcttgcaaca cagaaccaag a           21

<210> SEQ ID NO 11
<211> LENGTH: 40
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(40)
<223> OTHER INFORMATION: Template O42TCMB

<400> SEQUENCE: 11
tgctgttctg tgttgtcgtt ttttttgag ctcatgaggt           40

<210> SEQ ID NO 12
<211> LENGTH: 80
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(80)
<223> OTHER INFORMATION: Template O9TCSG

<400> SEQUENCE: 12
tataatcatt acatttacta cctttacttt ctactacttt tactctcctt tatctacatc           60
ccttttattg agctcatgag           80

<210> SEQ ID NO 13
<211> LENGTH: 12
<212> TYPE: DNA
<213> ORGANISM: Artificial Sequence
<220> FEATURE:
<223> OTHER INFORMATION: Unassigned DNA

```
<220> FEATURE:
<221> NAME/KEY: source
<222> LOCATION: (1)..(12)
<223> OTHER INFORMATION: Figure 2

<400> SEQUENCE: 13
attttctcta tg                                                               12

<210> SEQ ID NO 14
<211> LENGTH: 12
<212> TYPE: DNA
<213> ORGANISM: Artificial Sequence
<220> FEATURE:
<223> OTHER INFORMATION: Unassigned
<220> FEATURE:
<221> NAME/KEY: source
<222> LOCATION: (1)..(12)
<223> OTHER INFORMATION: Figure 3 first sequence

<400> SEQUENCE: 14
ctcagagaag ag                                                               12

<210> SEQ ID NO 15
<211> LENGTH: 21
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(21)
<223> OTHER INFORMATION: Figure 3, second sequence

<400> SEQUENCE: 15
attttttttc tctttgtttt t                                                     21

<210> SEQ ID NO 16
<211> LENGTH: 10
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(10)
<223> OTHER INFORMATION: Figure 3

<400> SEQUENCE: 16
taaaaaaaag                                                                  10

<210> SEQ ID NO 17
<211> LENGTH: 13
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(13)
<223> OTHER INFORMATION: Figure 3

<400> SEQUENCE: 17
taaaaaaaag aga                                                              13

<210> SEQ ID NO 18
<211> LENGTH: 21
<212> TYPE: DNA
<213> ORGANISM: Artificial Sequence
<220> FEATURE:
```

```
<223> OTHER INFORMATION: Unassigned DNA
<220> FEATURE:
<221> NAME/KEY: source
<222> LOCATION: (1)..(21)
<223> OTHER INFORMATION: Figure 3

<400> SEQUENCE: 18
taaaaaaaag agaaacaaaa a                                                 21

<210> SEQ ID NO 19
<211> LENGTH: 39
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(39)
<223> OTHER INFORMATION: Figure 4

<400> SEQUENCE: 19
attttctgtt ctgttgcttg cttcgttgct tcgttttcc                              39

<210> SEQ ID NO 20
<211> LENGTH: 23
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(23)
<223> OTHER INFORMATION: Figure 4

<400> SEQUENCE: 20
taaaagacaa gacaacgaac gaa                                               23

<210> SEQ ID NO 21
<211> LENGTH: 39
<212> TYPE: DNA
<213> ORGANISM: Artificial Sequence
<220> FEATURE:
<223> OTHER INFORMATION: Unassigned DNA
<220> FEATURE:
<221> NAME/KEY: source
<222> LOCATION: (1)..(39)
<223> OTHER INFORMATION: Figure 4

<400> SEQUENCE: 21
taaaagacaa gacaacgaac gaagcaacga agcaaaagc                              39
```